: US 9,895,270 B2

(12) United States Patent
Coward et al.

(10) Patent No.: US 9,895,270 B2
(45) Date of Patent: Feb. 20, 2018

(54) REDUCED-PRESSURE, ABDOMINAL TREATMENT SYSTEMS AND METHODS

(71) Applicant: KCI Licensing, Inc., San Antonio, TX (US)

(72) Inventors: Christopher Guy Coward, Wareham (GB); Mark Stephen James Beard, Ferndown (GB); Colin John Hall, Poole (GB); Ian James Hardman, Bournemouth (GB); Keith Patrick Heaton, Poole (GB); James Joseph Sealy, Hants (GB); David George Whyte, Wareham (GB)

(73) Assignee: KCI Licensing, Inc., San Antonio, TX (US)

( * ) Notice: Subject to any disclaimer, the term of this patent is extended or adjusted under 35 U.S.C. 154(b) by 545 days.

(21) Appl. No.: 14/078,140

(22) Filed: Nov. 12, 2013

(65) Prior Publication Data
US 2014/0068914 A1   Mar. 13, 2014

Related U.S. Application Data

(62) Division of application No. 12/467,211, filed on May 15, 2009, now Pat. No. 8,608,776.
(Continued)

(51) Int. Cl.
*A61F 13/00*      (2006.01)
*A61B 17/00*      (2006.01)
*A61M 1/00*       (2006.01)

(52) U.S. Cl.
CPC .... *A61F 13/00068* (2013.01); *A61B 17/0057* (2013.01); *A61F 13/00025* (2013.01);
(Continued)

(58) Field of Classification Search
CPC .......... A61F 13/00068; A61F 13/00072; A61F 13/00076; A61F 13/00085;
(Continued)

(56) References Cited

U.S. PATENT DOCUMENTS 1,355,846 A   10/1920  Rannells
2,547,758 A   4/1951   Keeling
(Continued)

FOREIGN PATENT DOCUMENTS

AU   550575 A1   3/1986
AU   745271      4/1999
(Continued)

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (copy and certified translation).
(Continued)

*Primary Examiner* — Jocelin Tanner

(57) ABSTRACT

A method of manufacturing a reduced-pressure abdominal treatment system for treating an open abdominal cavity of a patient is provided. A reduced-pressure abdominal treatment system has an open-cavity treatment device for providing reduced-pressure treatment to a patient's abdominal cavity; a deep-tissue closure device for applying a closing force on a deep-tissue wound on a patient's fascia; a surface-wound closure subsystem for providing a closing force on a surface wound on the patient's epidermis. The method of manufacturing may also include the step of providing a reduced-pressure supply subsystem.

22 Claims, 20 Drawing Sheets

Related U.S. Application Data

(60) Provisional application No. 61/109,486, filed on Oct. 29, 2008, provisional application No. 61/109,448, filed on Oct. 29, 2008, provisional application No. 61/109,410, filed on Oct. 29, 2008, provisional application No. 61/109,390, filed on Oct. 29, 2008.

(52) U.S. Cl.
CPC .. *A61F 13/00034* (2013.01); *A61F 13/00987* (2013.01); *A61M 1/0088* (2013.01); *A61B 2017/00575* (2013.01); *A61B 2017/00646* (2013.01); *A61B 2017/00676* (2013.01); *A61F 13/00029* (2013.01); *A61F 13/00038* (2013.01); *A61M 1/0092* (2014.02); *Y10T 29/49* (2015.01); *Y10T 29/49826* (2015.01); *Y10T 156/1052* (2015.01); *Y10T 156/1056* (2015.01); *Y10T 156/1057* (2015.01); *Y10T 156/1062* (2015.01); *Y10T 156/1304* (2015.01)

(58) Field of Classification Search
CPC .......... A61F 13/00089; A61F 13/00987; A61F 13/00025; A61F 13/00029; A61F 13/00; A61F 13/00004; A61F 13/00021; A61F 13/00038; A61F 13/00034; A61F 2013/00127; A61F 2013/0028; A61B 17/0057; A61B 2017/00646; A61B 2017/00676; A61B 2017/00575; A61M 1/0088; A61M 1/0092; Y10T 156/1057; Y10T 156/1304; Y10T 156/1056; Y10T 156/1062; Y10T 156/1052; Y10T 29/49826; Y10T 29/49
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,051,747 A * | 4/2000 | Lindqvist ............... A61F 13/02 602/41 |
| 6,071,267 A * | 6/2000 | Zamierowski ...... A61F 13/0203 604/289 |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,752,794 B2 * | 6/2004 | Lockwood .......... A61M 1/0058 604/313 |
| 6,814,079 B2 | 11/2004 | Heaton et al. |
| 7,790,945 B1 * | 9/2010 | Watson, Jr. ......... A61F 13/0203 602/43 |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2004/0030304 A1 * | 2/2004 | Hunt ................... A61M 1/0088 604/317 |
| 2004/0073151 A1 * | 4/2004 | Weston ................ A61F 15/008 602/41 |

(56) References Cited

U.S. PATENT DOCUMENTS

| | | | |
|---|---|---|---|
| 2005/0148913 A1* | 7/2005 | Weston | A61M 1/0088 602/2 |
| 2006/0079852 A1 | 4/2006 | Bubb et al. | |
| 2006/0282028 A1* | 12/2006 | Howard | A61M 27/00 602/2 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 3/1999 |
| WO | 80/02182 A1 | 10/1980 |
| WO | 87/04626 A1 | 8/1987 |
| WO | 90/10424 A1 | 9/1990 |
| WO | 93/09727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, YU. A., et al; "Vacuum Therapy in the Treatment of Purulent Lactation Mastitis"; Vestnik Khirurgi, May 14, 1986, pp. 66-70, and 9 page English translation thereof.
Yusupov. YU. N., et al; "Active Wound Drainage", Vestnik Khirurgi, vol. 138, Issue 4, 1987, and 7 page English translation thereof.
Davydov, YU. A., et al; "Bacteriological and Cytological Assessment of Vacuum Therapy for Purulent Wounds"; Vestnik Khirurgi, Oct. 1988, pp. 48-52, and 8 page English translation thereof.
Davydov, YU. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Bjorn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Ðukić, Ž. Maksimović, Ð. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract,

(56) References Cited

OTHER PUBLICATIONS editor-in-chief Prov. V.I. Parahonyak (S.M. Kirov Gorky State Medical Institute, Gorky, U.S.S.R. 1987) ("Solovev Guidelines")

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians (Jul. 2007).

\* cited by examiner

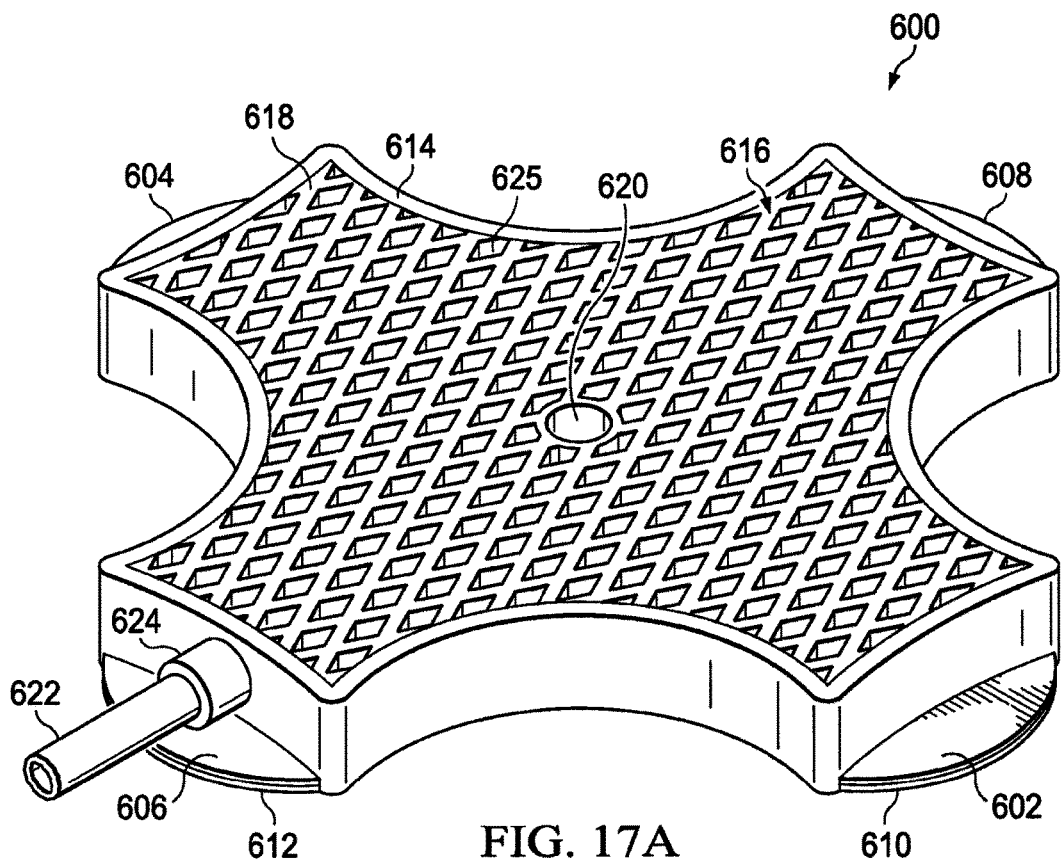
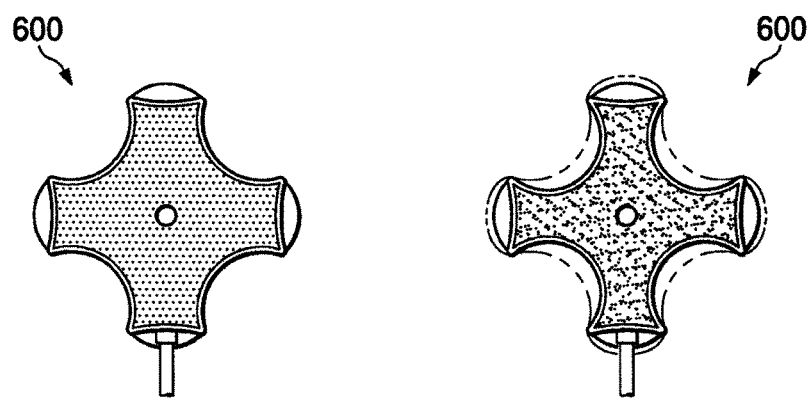
FIG. 17A
FIG. 17B  FIG. 17C

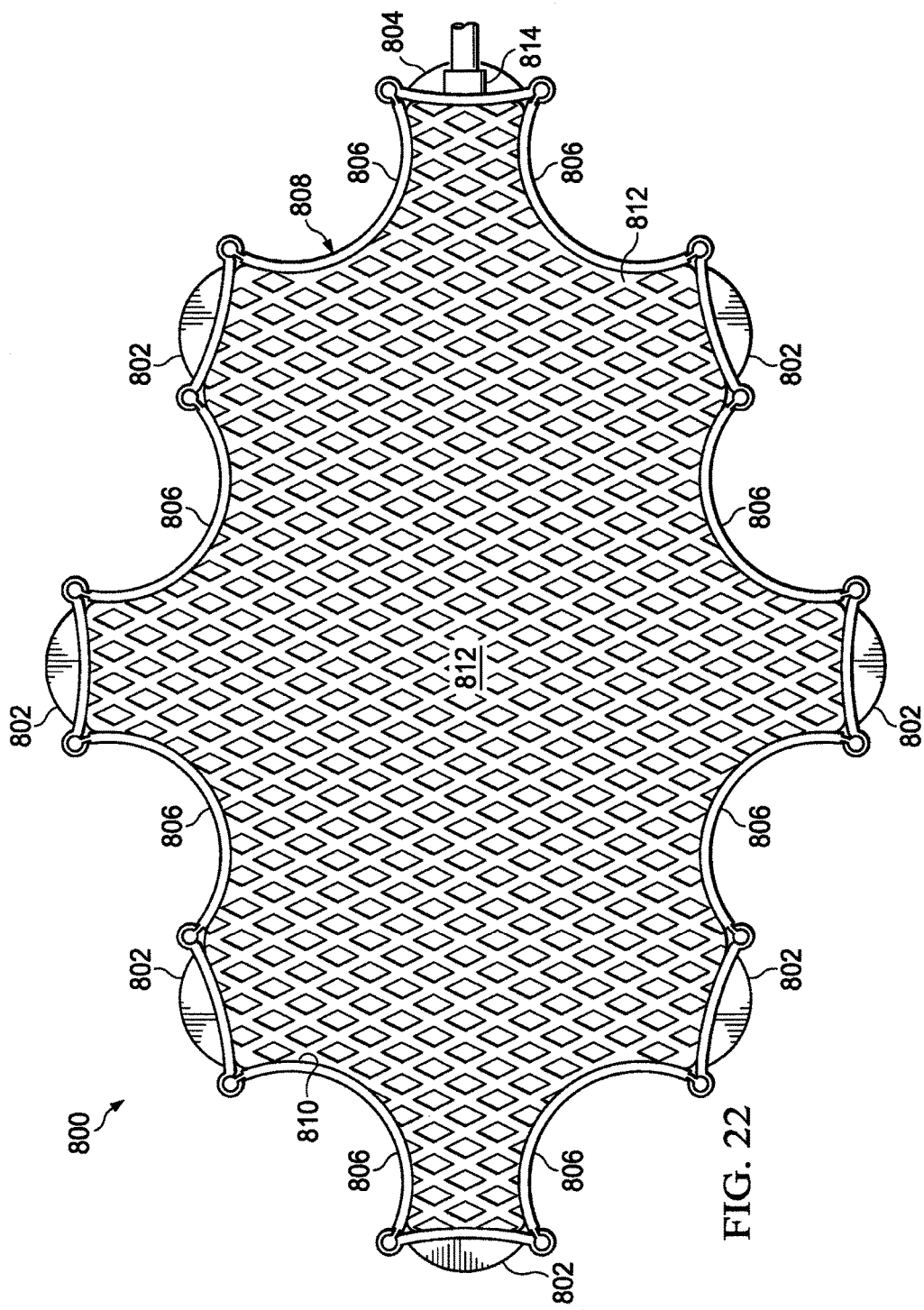

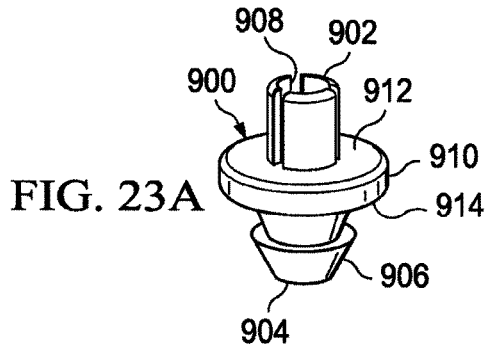
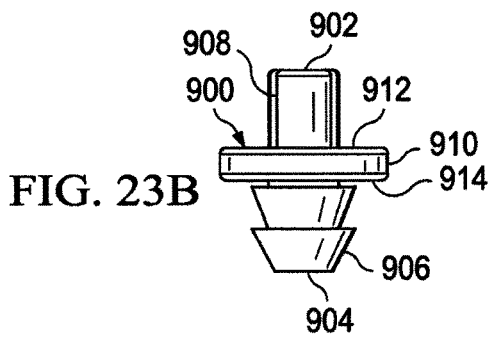
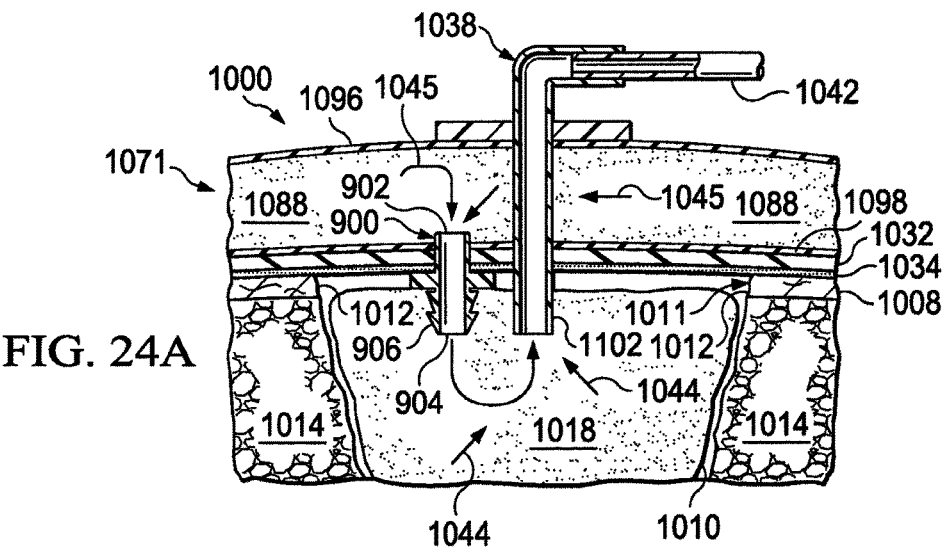
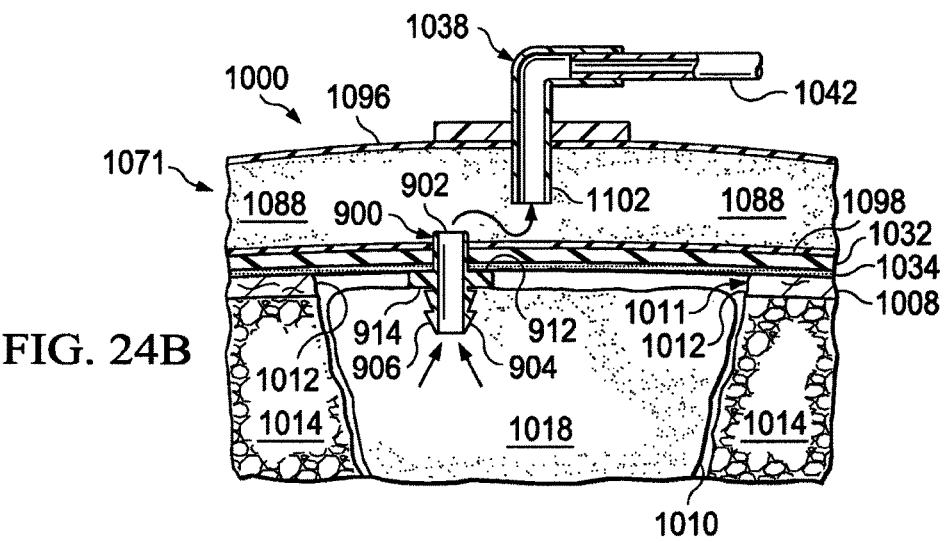

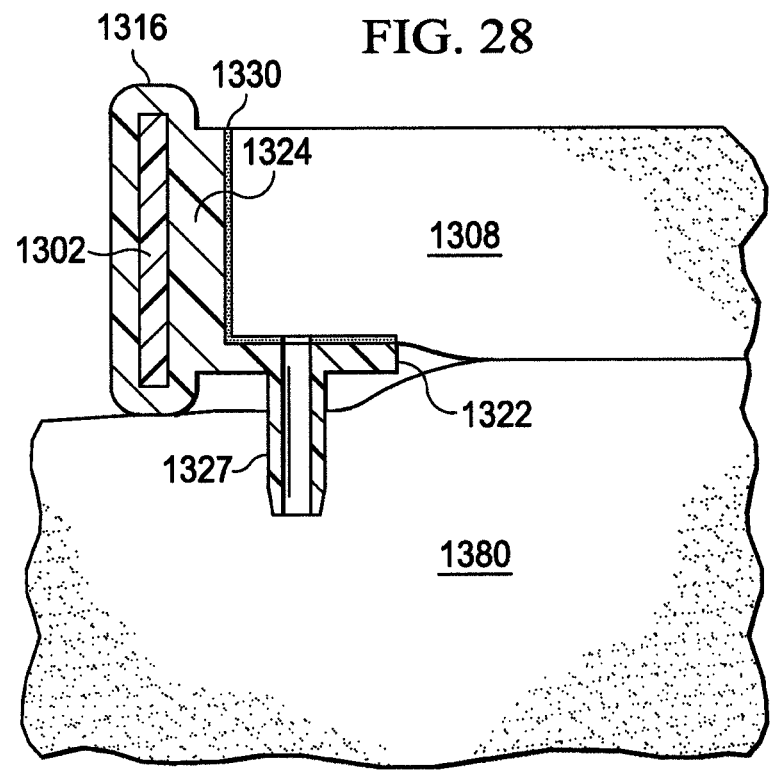
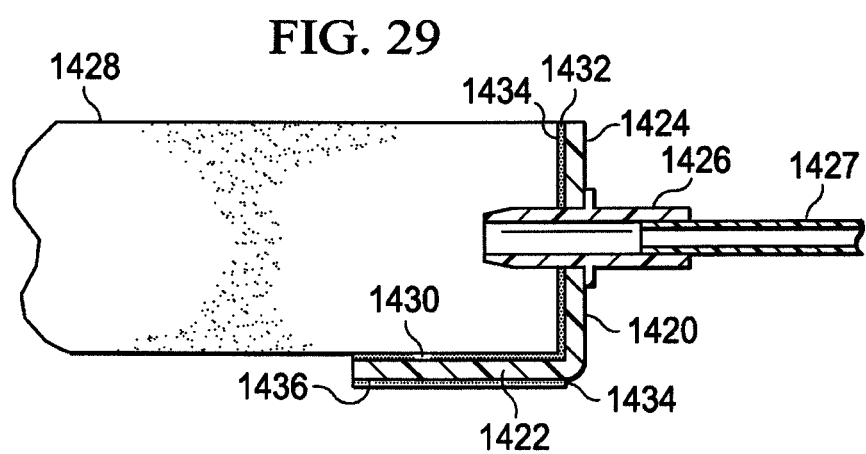

REDUCED-PRESSURE, ABDOMINAL TREATMENT SYSTEMS AND METHODS

RELATED APPLICATIONS

This application is a divisional of U.S. application Ser. No. 12/467,211, filed May 15, 2009, which claims the benefit of the filing of U.S. Provisional Patent Application Ser. No. 61/109,486, entitled "Reduced-Pressure, Abdominal Treatment System and Method," filed Oct. 29, 2008; U.S. Provisional Patent Application Ser. No. 61/109,448, entitled "Reduced-Pressure, Deep-Tissue Closure System and Method," filed Oct. 29, 2008; U.S. Provisional Patent Application Ser. No. 61/109,410, entitled "Reduced-Pressure, Wound-Closure System and Method," filed Oct. 29, 2008; and U.S. Provisional Patent Application Ser. No. 61/109,390, entitled "Open-Cavity, Reduced-Pressure Wound Dressing and System," filed Oct. 29, 2008. Priority is claimed to all of the above-mentioned applications, and each application is hereby incorporated by reference.

BACKGROUND

The present invention relates generally to medical treatment systems and, more particularly, to reduced-pressure, abdominal treatment systems and methods.

Whether the etiology of a wound, or damaged area of tissue, is trauma, surgery, or another cause, proper care of the wound is important to the outcome. Unique challenges exist when the wound involves locations that require reentry, for example, the peritoneal cavity and more generally the abdominal cavity. Often times when surgery or trauma involves the abdominal cavity, establishing a wound management system that facilitates reentry allows for better and easier care and helps to address such things as peritonitis, abdominal compartment syndrome (ACS), and infections that might inhibit final healing of the wound and the internal organs. In providing such care, it may be desirable to remove unwanted fluids from the cavity, help approximate the fascia and other tissues, and finally to help provide a closing force on the wound itself at the level of the epidermis.

Currently, an abdominal opening on the epidermis may be closed using sutures, staples, clips, and other mechanical devices to allow the skin, or epidermis, to be held and pulled. Such devices often cause puncture wounds or other wounds. If severe edema occurs, tremendous pressure may be placed on the closure device with potential harm resulting. For example, if the pressure rises due to edema, the sutures may tear out.

With respect to the overall system for allowing reentry into the abdominal cavity, a number of techniques have been developed. One approach is to place towels down into the abdominal cavity and then use clips, such as hemostats, to close the skin over the towels. While simple and fast, the results have been regarded as suboptimal. Another approach is the "Bogota bag." With this approach, a bag is sutured into place to cover the open abdomen in order to provide a barrier. Still another approach, sometimes called a "vac pack," has been to pack towels in the wound and then place a drain into the abdomen and cover the abdomen with a drape. Finally, a reduced pressure approach has been used. Such an approach is shown in U.S. Pat. No. 7,381,859 to Hunt et al. and assigned to KCI Licensing, Inc. of San Antonio, Tex. U.S. Pat. No. 7,381,859 is incorporated herein by reference for all purposes.

A number of deep tissues, e.g., fat, muscle, or particularly fascia, may be addressed when one is temporarily closing the abdomen. Unless otherwise indicated, as used herein, "or" does not require mutual exclusivity. If not addressed, the deep tissue may retract further into the abdominal cavity and subsequently cause difficulties. The surgeon may suture the deep tissue, e.g., the fascia, while placing the fascia under tension. This can be problematic, however, if reduced-pressure treatment in the area is desired or if the dressing needs to be replaced. Moreover, suturing the deep tissue can at times cause necrosis. At the same time, if the deep tissue, notably the fascia, is not closed, this situation can lead to hernias and other complications.

In addition to accessing the abdominal cavity for reentry, it is desirable to remove fluids. It may also be desirable to provide reduced-pressure therapy to the tissue site, including wounds that may be within the abdominal cavity. Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "topical negative pressure," "reduced pressure therapy," or "vacuum therapy") provides a number of benefits, including faster healing and may increase formulation of granulation tissue.

SUMMARY

Problems with existing abdominal treatment systems and methods are addressed by the systems, apparatus, and methods of the illustrative embodiments described herein. According to one illustrative embodiment, a reduced-pressure abdominal treatment system includes an open-cavity treatment device for providing reduced-pressure treatment proximate a patient's abdominal contents; a deep-tissue closure device for applying a closing force on a deep-tissue, e.g., a patient's fascia; and a reduced-pressure treatment subsystem for providing reduced-pressure treatment in the patient's abdominal cavity. The reduced-pressure treatment system may also include a surface-wound closure subsystem for providing a closing force on the patient's epidermis. The reduced-pressure treatment system may also include a reduced-pressure supply subsystem operable to develop reduced pressure for use in the open-cavity treatment device, deep-tissue closure device, the reduced-pressure treatment subsystem, and the surface-wound closure subsystem.

According to another illustrative embodiment, a method of treating an open abdominal cavity includes the step of disposing in the abdominal cavity an open-cavity treatment device, which has a first side and a second, inward-facing side. The second, inward-facing side of the open-cavity treatment device is disposed proximate the patient's abdominal contents. The method of treating an open abdominal cavity further includes the step of disposing in the open abdominal cavity a deep-tissue closure device, which has a first side and a second, inward-facing side. The deep-tissue closure device is disposed with the second, inward-facing side of the deep-tissue closure device proximate the first side of the open-cavity treatment device and the first side of the deep-tissue closure device proximate the fascia. The method of treating an open abdominal cavity may further include the steps of disposing a manifold within the patient's abdominal cavity; forming a pneumatic seal over the patient's abdominal cavity; fluidly coupling a first reduced-pressure interface to the manifold; releasably attaching a first attachment member to a first portion of the patient's epidermis proximate an edge of the surface wound; and releasably attaching a second attachment member to a second portion of the patient's epidermis proximate the edge of the surface wound. The first attachment member is spaced from the second attachment member. The method of treating an open abdominal cavity further includes the steps of providing a sealed contracting member coupled to the first attachment member and the second attachment member and operable to contract when placed under reduced pressure; and supplying reduced pressure to the open-cavity treatment device, the deep-tissue closure device, the manifold, and the sealed contracting member.

According to another illustrative embodiment, a method of manufacturing a system for treating an open abdominal cavity of a patient includes the steps of forming an open-cavity treatment device for providing reduced-pressure treatment to a patient's abdominal cavity; forming a deep-tissue closure device for applying a closing force on a deep-tissue wound on a patient's fascia; and forming a surface-wound closure subsystem for providing a closing force on a surface wound on the patient's epidermis. The method of manufacturing may also include the step of providing a reduced-pressure supply subsystem.

Other objects, features, and advantages of the illustrative embodiments will become apparent with reference to the drawings and detailed description that follow.

BRIEF DESCRIPTION OF THE DRAWINGS

FIG. 10 is a schematic, cross-sectional view of a detail of the illustrative deep-tissue closure subsystem of FIG. 1;

FIG. 17A is a schematic, perspective view of an illustrative embodiment of a reduced-pressure, surface-wound closure subsystem;

FIGS. 17B and 17C are schematic, plan views of the reduced-pressure, surface-wound closure system of FIG. 17A shown in a non-contracted position (FIG. 17B) and a contracted position (FIG. 17C);

FIG. 22 is schematic, perspective view of an illustrative embodiment of a modular, reduced-pressure, surface-wound closure subsystem;

FIG. 23A is a schematic, perspective view of an illustrative reduced-pressure connector;

FIG. 23B is an elevational view of the reduced-pressure connector of FIG. 23A;

FIG. 24A is a schematic, cross-sectional view of a portion of another illustrative embodiment of a reduced-pressure, wound-closure and treatment system;

FIG. 24B is a schematic, cross-sectional view of a portion of another illustrative embodiment of a reduced-pressure, wound-closure and treatment system;

FIG. 28 is a schematic, cross-sectional view of an illustrative embodiment of a portion of an illustrative embodiment of a sealed contracting member; and FIG. 29 is a schematic, cross-sectional view of an illustrative embodiment of an attachment member.

DETAILED DESCRIPTION OF ILLUSTRATIVE EMBODIMENTS

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

System Introduction

Figure 1:
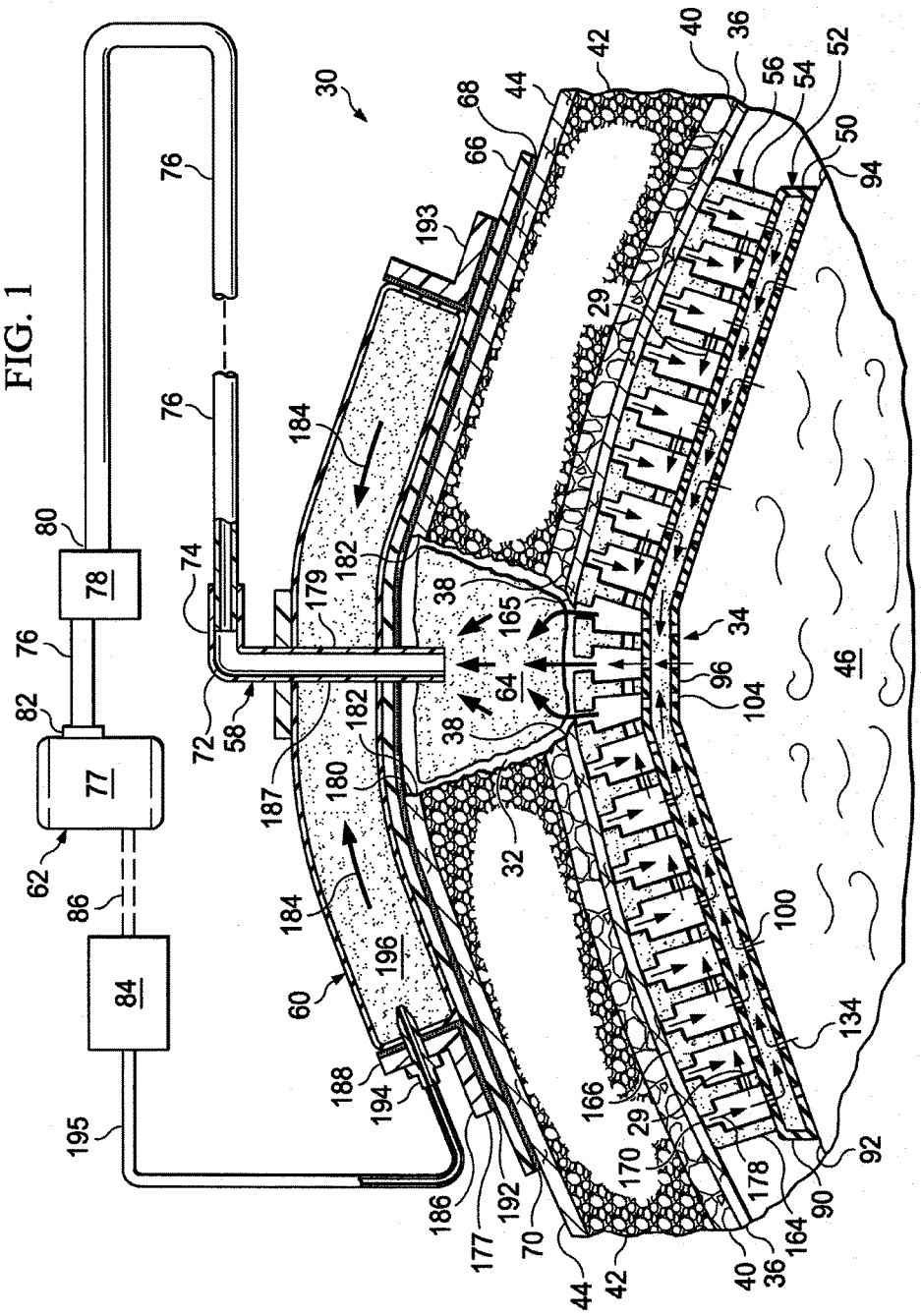
FIG. 1 is a schematic, cross sectional view, with a portion in block diagram, of an illustrative reduced-pressure, abdominal treatment system.
Figure 2:
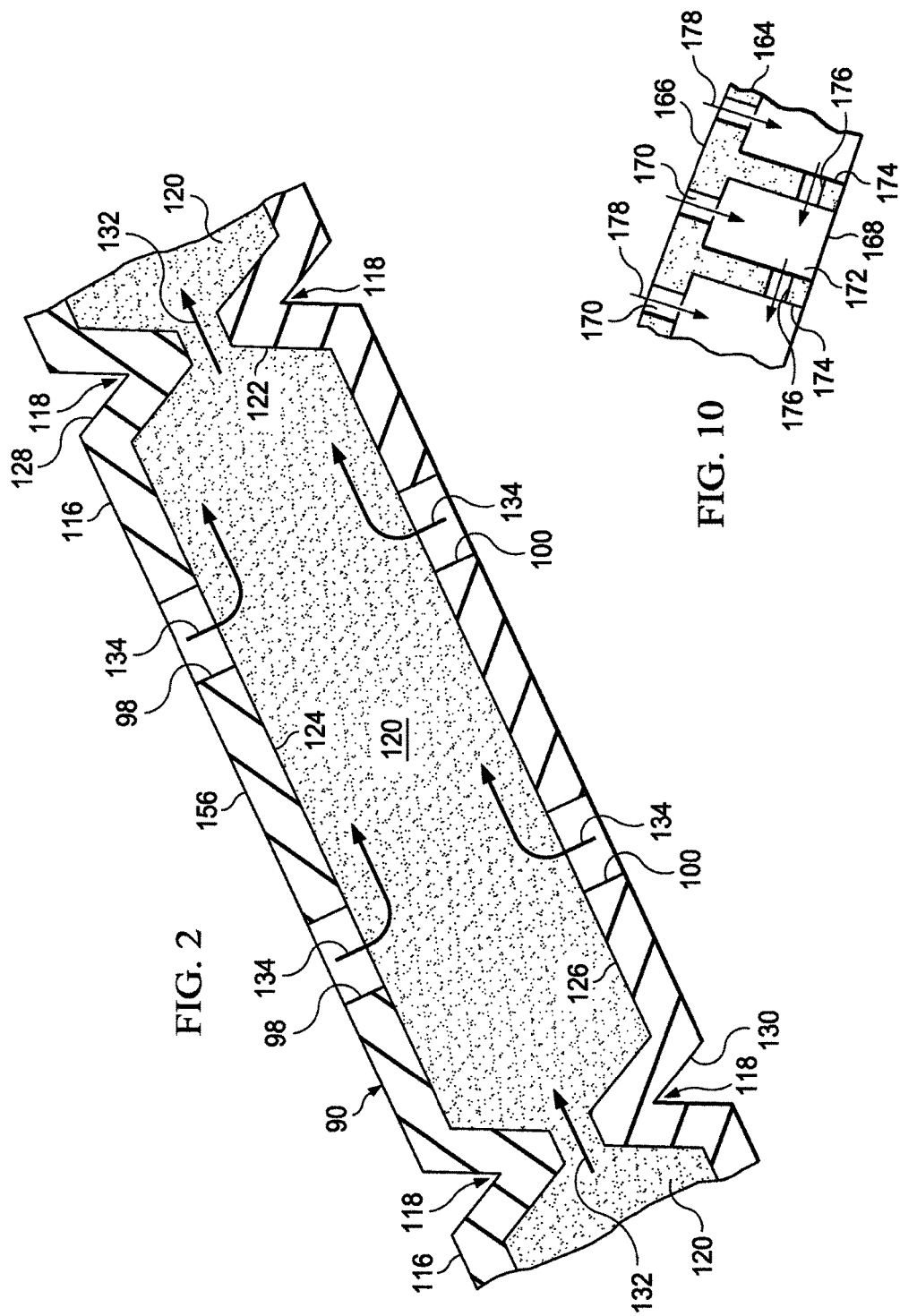
FIG. 2 is a schematic cross section of a portion of the illustrative reduced-pressure, abdominal treatment system of FIG. 1 showing a portion of an encapsulated leg member.

Referring primarily to FIG. 1, an illustrative embodiment of a reduced-pressure, abdominal treatment system 30 is presented. The reduced-pressure, abdominal treatment system 30 is for use in treating, or managing, a patient's abdominal cavity 32 and tissue or wounds associated with an open abdomen. As used herein, "wound" signifies a damaged area of tissue. The reduced-pressure, abdominal treatment system 30 may be used to treat a general tissue site 34; a deep-tissue wound in a deep tissue, such as in fascia 36, muscle 40, fat layer 42; and a surface wound 180 in epidermis 44. The wound in the fascia 36 has fascia edges 38. The surface wound 180 in the epidermis 44 has surface-wound edges 182. The tissue site 34 is shown on or proximate abdominal contents 46. The tissue site 34 may be the bodily tissue of any human, animal, or other organism. In this embodiment, the tissue site 34 generally includes tissue in the abdominal cavity 32 and typically tissue proximate the abdominal contents 46.

The reduced-pressure, abdominal treatment system 30 includes an open-cavity treatment device 50 that is part of an open-cavity treatment subsystem 52. The open-cavity treatment subsystem 52 helps provide reduced-pressure treatment in the patient's abdominal cavity 32 and provides a non-adherent cover for the abdominal contents 46. The reduced-pressure, abdominal treatment system 30 also includes a deep-tissue closure device 54 that is part of a deep-tissue closure subsystem 56. The deep-tissue closure subsystem 56 applies a closing force on a tissue and is particularly well suited for providing a closing force on a deep tissue, e.g., the fascia 36. The deep-tissue closure subsystem 56 may help approximate the fascia edges 38. The reduced-pressure, abdominal treatment system 30 also provides general reduced-pressure treatment with a reduced-pressure treatment subsystem 58. The surface wound 180 on the epidermis 44, and particularly the surface-wound edges 182, may be urged toward a central portion, or towards each other, by a closing force developed by a surface-wound closure subsystem 60. Finally, the reduced-pressure, abdominal treatment system 30 may include a reduced-pressure supply subsystem 62 that provides reduced pressure to various devices and subsystems within the reduced-pressure, abdominal treatment system 30. Each of the devices and subsystems will be described in more detail further below.

The reduced pressure delivered by the reduced-pressure, abdominal treatment system 30 may be applied in the abdominal cavity 32 and to tissue site 34 to help promote removal of exudates, ascites, or other liquids, bacteria, fibrin, dead tissue, toxins, residual blood, etc. In some instances reduced pressure may be applied to stimulate the growth of additional tissue, and in some instances, only fluid removal may be desired. In the case of a wound at the tissue site 104, the growth of granulation tissue and removal of exudates and bacteria may help to promote healing of the wound. As used herein, "reduced pressure" generally refers to a pressure less than the ambient pressure at the tissue site 34 that is being subjected to treatment. In most cases, this reduced pressure will be less than the atmospheric pressure at which the patient is located. Alternatively, the reduced pressure may be less than a hydrostatic pressure of tissue at the tissue site 34. Unless otherwise indicated, values of pressure stated herein are gauge pressures.

Reduced-Pressure Treatment Subsystems

An illustrative embodiment of a reduced-pressure subsystem, e.g., the reduced-pressure subsystem 58, will now be presented. The reduced-pressure treatment subsystem 58 includes a manifold 64, a sealing member 66 (or overdrape), and a reduced-pressure interface 72. The manifold 64 is shown disposed within the abdominal cavity 32. The sealing member 66 is placed over the surface wound 180 on the epidermis 44 to form a pneumatic seal over the abdominal cavity 32.

The manifold 64 may take many forms. The term "manifold" as used herein generally refers to a substance or structure that is provided to assist in applying reduced pressure to, delivering fluids to, or removing fluids from a tissue site, e.g., tissue site 34. The manifold 64 typically includes a plurality of flow channels or pathways that distribute fluids provided to and removed from the area of tissue around the manifold 64. The manifold 64 may include a plurality of flow channels or pathways that are interconnected to improve distribution of fluids. The manifold 64 may be a biocompatible material that is capable of being placed in contact with tissue and distributing reduced pressure. Examples of manifold 64 include, without limitation, devices that have structural elements arranged to form flow channels, cellular foam, such as open-cell foam, porous tissue collections, and liquids, gels and foams that include or cure to include flow channels. The manifold 64 may be porous and may be made from foam, gauze, felted mat, or any other material suited to a particular biological application. In one embodiment, the manifold 64 is porous foam and includes a plurality of interconnected cells or pores that act as flow channels. The porous foam may be a polyurethane, open-cell, reticulated foam, such as a GranuFoam® material provided by Kinetic Concepts, Incorporated of San Antonio, Tex. Other embodiments might include "closed cells" to direct fluid flow in the manifold 64. In some situations, the manifold 64 may also be used to distribute fluids, such as medications, antibacterials, growth factors, and other solutions into the abdominal cavity 32 or at the tissue site 34. Other layers may be included in the manifold 64, such as an absorptive material, wicking material, hydrophobic material, or hydrophilic material.

The sealing member 66 is placed over the abdominal cavity 32 and the surface wound 180 to provide a pneumatic seal between the sealing member 66 and the patient's epidermis 44. The pneumatic seal is adequate for reduced-pressure, abdominal treatment system 30 to hold reduced pressure at the tissue site 34. The sealing member 66 may be used to secure the manifold 64 on a central connection member 96 or on a portion of the deep-tissue closure subsystem 56 as shown in FIG. 1. While the sealing member 66 may be impermeable or semi permeable, the sealing member 66 is capable of maintaining reduced pressure at the tissue site 34 after installation of the sealing member 66 and other system compenents. The sealing member 66 may be a flexible over-drape, cover, or film formed from a silicone based compound, acrylic, hydrogel or hydrogel-forming material, or any other biocompatible material that includes the impermeability or permeability characteristics desired for the tissue site.

The sealing member 66 may further include an attachment device 68 to secure the sealing member 66 to the patient's epidermis 44 or to a gasket member around the surface-wound edges 182. The attachment device 68 may take many forms; for example, an adhesive 70 may be positioned along a perimeter of the sealing member 66 or any portion of the sealing member 66 to provide, directly or indirectly, the pneumatic seal with the patient's epidermis 44. The adhesive 70 might also be pre-applied and covered with a releasable backing, or member, that is removed at the time of application.

The reduced-pressure interface 72 permits the passage of fluid from the manifold 64 to a first reduced-pressure delivery conduit 76 and vice versa. The reduced-pressure interface 72 may be, as one example, a port or connector 74. Thus, fluids collected from the abdominal cavity 32 using the manifold 64 may enter the first reduced-pressure delivery conduit 76 via the reduced-pressure interface 72. In another embodiment, the reduced-pressure, abdominal treatment system 30 may exclude the reduced-pressure interface 72 and the first reduced-pressure delivery conduit 76 may be inserted directly into the sealing member 66 and into the manifold 64. The first reduced-pressure delivery conduit 76 may be a medical conduit or tubing or any other means for transporting a reduced pressure. The first reduced-pressure delivery conduit 76 may be a multi-lumen member for readily delivering reduced pressure and removing fluids. In one embodiment, the first reduced-pressure delivery conduit 76 is a two-lumen conduit with one lumen for fluid transport and one for pressure sensing in fluid communication with a pressure sensor. In another embodiment, the first reduced-pressure conduit 76 may be two separate conduits or a single conduit having two or more lumens.

Reduced pressure may be supplied to the first reduced-pressure delivery conduit 76 by the reduced-pressure supply subsystem 62, which includes a reduced-pressure source 77. A wide range of reduced pressures may be developed, such as from −50 mm Hg. to −500 mm Hg and more typically in the range of −100 mm Hg to −300 mm Hg. The pressure developed may be constant or varied over time. In one illustrative embodiment, the reduced-pressure source 77 includes preset selectors for −100 mm Hg, −125 mm Hg, and −150 mm Hg. The reduced-pressure source 77 may also include a number of alarms, such as a blockage alarm, a leakage alarm, a canister full alarm, or a battery-low alarm. The reduced-pressure source 77 could be a portable source, a wall source, a vacuum pump or other unit. The reduced-pressure supply subsystem 62 may need to accommodate fluid removal of as much as five liters or more per day.

A number of different devices, e.g., representative device 78, might be added to a medial portion 80 of the first reduced-pressure-delivery conduit 76. For example, the representative device 78 may be a fluid reservoir, or canister collection member, a pressure-feedback device, a volume detection system, a blood detection system, an infection detection system, a filter, a port with a filter, a flow monitoring system, a temperature monitoring system, etc. Multiple devices, e.g., representative device 78 may be included. Some of these devices, e.g., the fluid collection member, may be formed integrally with the reduced-pressure source 77. For example, a reduced-pressure port 82 on the reduced-pressure source 77 may include a filter member (not shown) that includes one or more filters and may include a hydrophobic filter that prevents liquid from entering an interior space.

Open-Cavity Treatment Subsystems and Treatment Devices

The open-cavity treatment subsystem 52 is for treating the abdominal cavity 32 or the tissue site 34. The open-cavity treatment subsystem 52 will now be presented in more detail.

Referring to FIGS. 1-5, the open-cavity treatment subsystem 52 includes the open-cavity treatment device 50 that is disposed within the abdominal cavity 32. The open-cavity treatment device 50 includes a plurality of encapsulated leg members 90 that may be coupled to a non-adherent drape 108. The non-adherent drape and plurality of encapsulated leg members 90 are supported by the abdominal contents 46. One or more of the plurality of encapsulated leg members 90 may be placed in or proximate a first paracolic gutter 92, and one or more of the plurality of encapsulated leg members 90 may be placed in or proximate a second paracolic gutter 94. Alternatively or in addition, the plurality of encapsulated leg members 90 may be placed at other desired locations, e.g., pelvic cavity, behind the liver, etc. Each of the plurality of encapsulated leg members 90 are coupled to the central connection member 96. The plurality of encapsulated leg members 90 and the central connection member 96 are in fluid communication. Both the plurality of encapsulated leg members 90 and the central connection member 96 are formed with fenestrations 98, 100, 102, 104 that allow fluids in the abdominal cavity 32 to pass. The fenestrations 98, 100, 102, 104 may take any shape, such as circular openings, rectangular openings, polygons, etc., but are presented in this illustrative embodiment as slits (elongated openings).

The open-cavity treatment device 50 includes the non-adherent drape 108 that may be formed of any non-adherent film material that helps prevent tissue from adhering to the non-adherent drape 108. In one embodiment, the non-adherent drape 108 is formed from a breathable polyurethane film. The non-adherent drape 108 is formed with a plurality of fenestrations 110, which may take any shape. The open-cavity treatment device 50 includes the central connection member 96 to which the plurality of encapsulated leg members 90 are coupled. The central connection member 96 may be encapsulated, including the edges of the central connection member 96, except at leg coupling areas 112 that allow fluid communication with the encapsulated leg members 90. The central connection member 96 has apertures or fenestrations, e.g., apertures 104, which allow fluid communication between a connection manifold member 114 and the manifold 64. The fluid communication between the connection manifold member 114 and the manifold 64 may be via the deep-tissue closure device 54.

Each of the encapsulated leg members 90 may be formed with a plurality of defined leg modules, such as leg modules 116. A manipulation zone 118 may be located between adjacent leg modules 116. The manipulation zones 118 facilitate movement of the open-cavity treatment device 50 and cutting of the open-cavity treatment device 50 to size the open-cavity treatment device 50.

Each encapsulated leg member 90 has a leg manifold member 120, which may be a single manifold member that runs between the leg modules 116 or may be formed with discrete components of a manifold material that make up the leg manifold member 120. The leg manifold member 120 is disposed within an interior portion 122 of the encapsulated leg member 90. The leg manifold member 120 has a first side 124 and second, inward-facing (patient-facing) side 126. A first leg encapsulating member 128, which is formed with the fenestrations 98, is disposed on the first side 124 of the leg manifold member 120. Similarly, a second leg encapsulating member 130, which has fenestrations 100, is disposed on the second, inward-facing side 126 of the leg manifold member 120. The second leg encapsulating member 130 may be a portion of the non-adherent drape 108. As shown in the longitudinal cross section of FIG. 2 by arrows 132, fluid may flow between the adjacent leg modules 116.

As shown by arrows 134, fluid is able to enter the fenestrations 98 and 100 and flow into the leg manifold member 120 and then flow toward the central connection member 96 as represented by the flow arrows 132.

Figure 3:
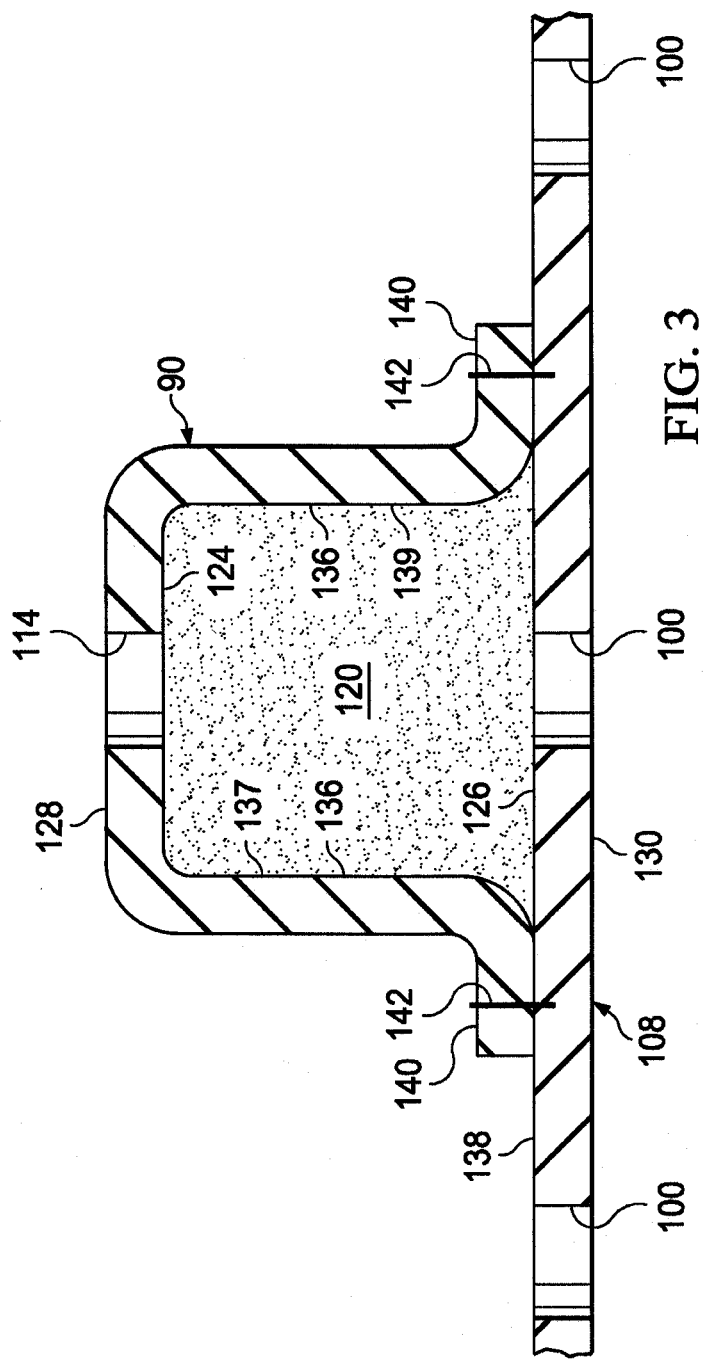
FIG. 3 is a schematic cross section of a portion of the illustrative reduced-pressure, abdominal treatment system of FIG. 1 showing a portion of an encapsulated leg member.

Referring now primarily to FIG. 3, a lateral cross section of the encapsulated leg member 90 is presented. As before, it can be seen that the first side 124 of the leg manifold member 120 is covered with the first leg encapsulating member 128 and that the second, inward-facing side 126 of the leg manifold member 120 is covered by the second leg encapsulating member 130. It should be noted that the first leg encapsulating member 128 and the second leg encapsulating member 130 may be a single sheet folded over the leg manifold member 120 and sealed. In the illustrative embodiment, the second leg encapsulating member 130 is a portion of the non-adherent drape 108. The leg manifold member 120 has peripheral edges 136 that are also covered by a portion of the first leg encapsulating member 128. The peripheral edges 136 include a first lateral edge 137 and a second lateral edge 139. The first leg encapsulating member 128 covers the first side 124 and the peripheral edges 136 and extends onto a first surface 138 of the non-adherent drape 108 and thereby forms extensions 140. The extensions 140 are coupled to the second leg encapsulating member 130 by any attachment device, e.g., welding (e.g., ultrasonic or RF welding), bonding, adhesives, cements, etc., and in this example by welds 142.

Figure 4:
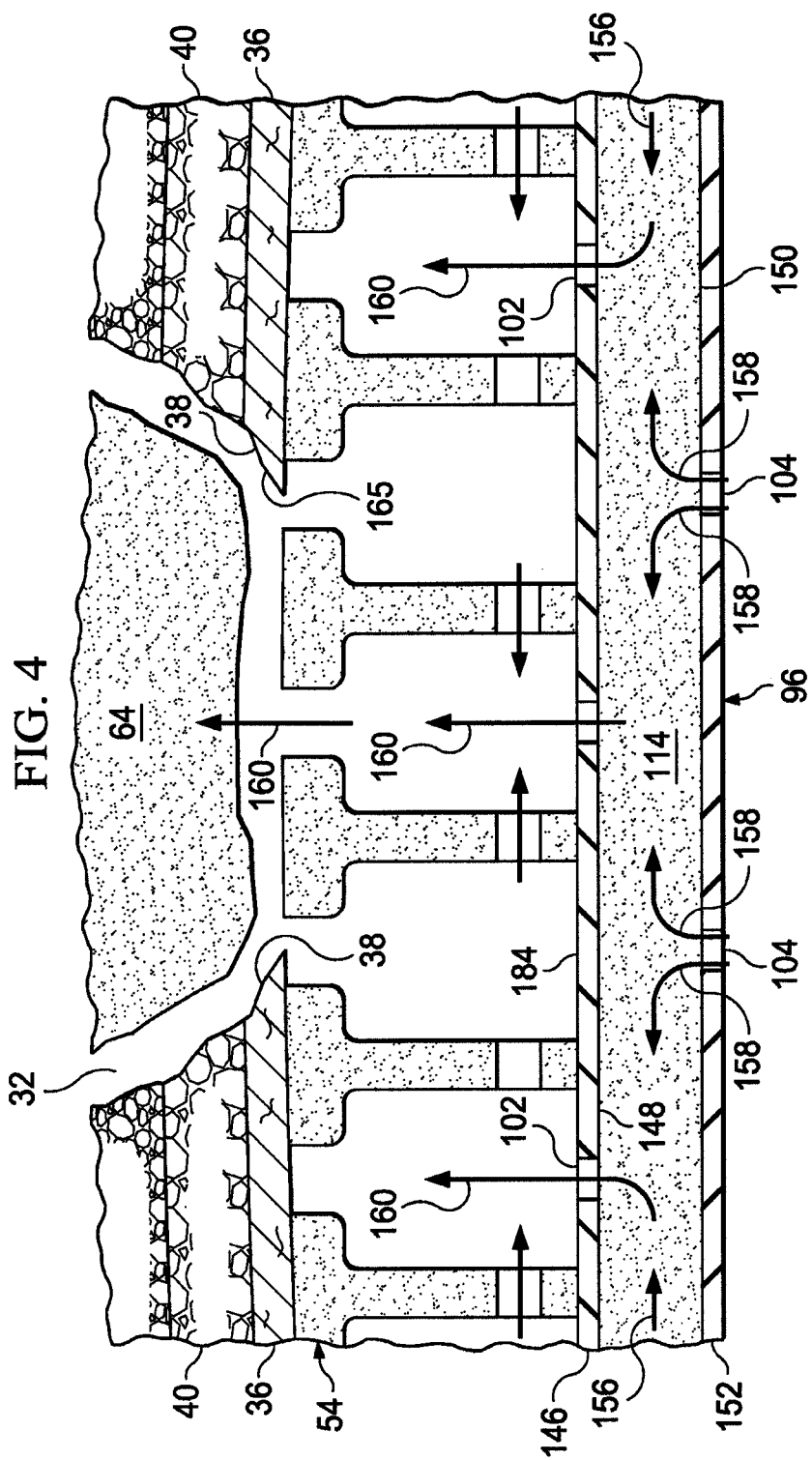
FIG. 4 is a schematic cross section of a portion of the illustrative reduced-pressure, abdominal treatment system of FIG. 1 showing a central connection member.
Figure 5:
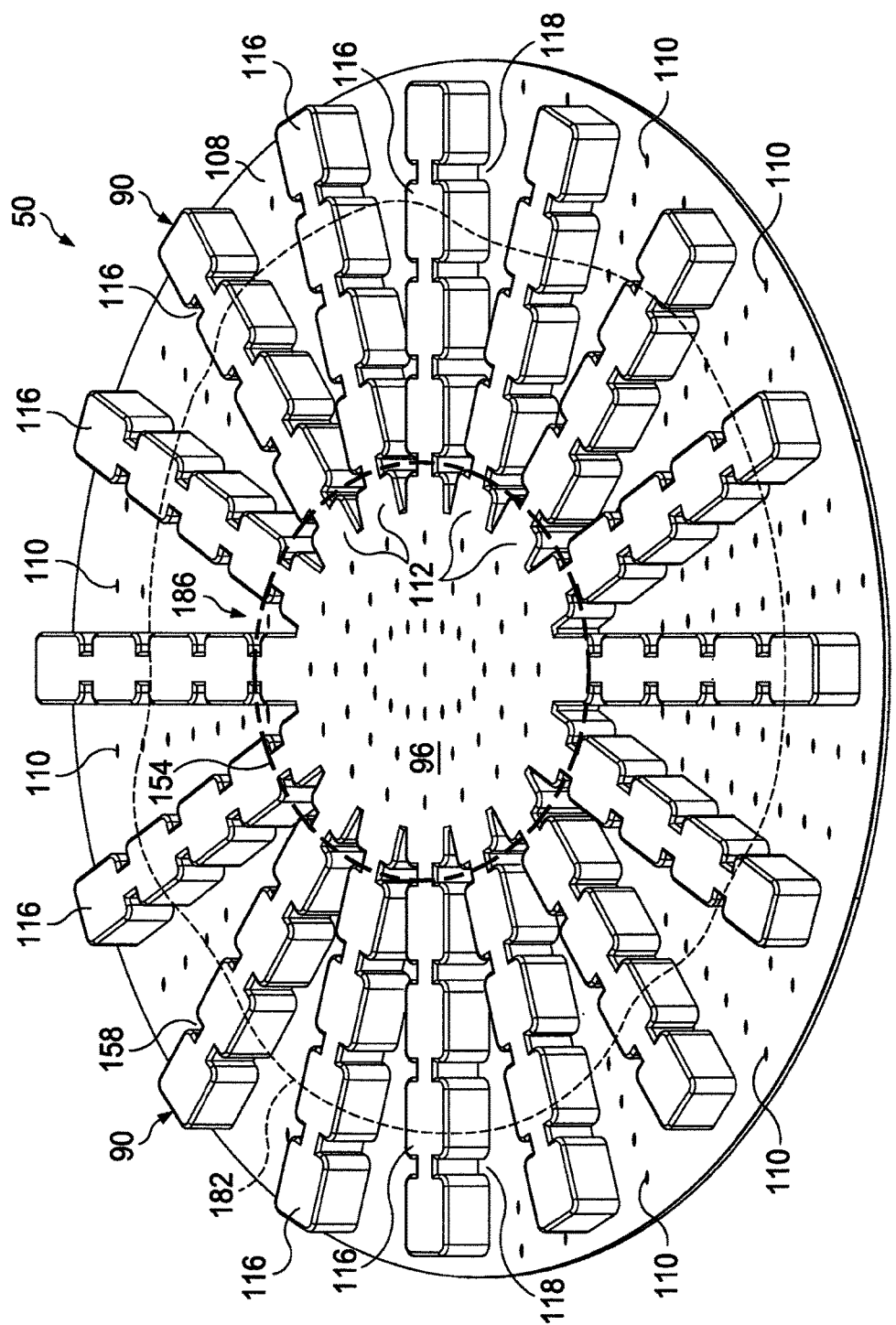
FIG. 5 is a schematic, perspective view of the open-cavity, reduced-pressure treatment device of FIG. 1.

Referring now primarily to FIG. 4, a schematic cross section of a portion of the central connection member 96 is shown. The central connection member 96 is formed with the connection manifold member 114 that is encapsulated with a first connection encapsulation member 146, which has fenestrations 102, and a second connection encapsulation member 152, which has fenestrations 104. The first connection encapsulation member 146 is disposed on a first side 148 of the connection manifold member 114. A second, inward-facing side 150 of connection manifold member 114 has the second connection encapsulation member 152 disposed proximate to the second, inward-facing side 150. With reference primarily to FIGS. 4 and 5, the first connection encapsulation member 146 has a peripheral edge 154. In a similar fashion, the second connection encapsulation member 152 has a peripheral edge that corresponds with the peripheral edge 154 of the first connection encapsulation member 146. The peripheral edge 154 of the first connection encapsulation member 146 is coupled to the peripheral edge of the second connection encapsulation member 152, except at the leg coupling areas 112 in order to provide flow channels for fluid within the encapsulated leg members 90 to flow into the connection manifold member 114 as suggested by reference arrows 156 in FIG. 4. Fluid may also enter directly into the connection manifold member 114 by flowing through the fenestrations 104 as suggested by arrows 158.

The deep-tissue closure device 54 is deployed proximate to the first connection encapsulation member 146. When reduced pressure is applied to the manifold 64, the reduced pressure is communicated through the deep-tissue closure device 54 and that causes fluid to flow from the connection manifold member 114 through the fenestrations 102, through the deep-tissue closure device 54, and into the manifold 64 as is suggested by arrows 160. The fluid continues to flow in the direction of the reduced-pressure interface 72 and from there flows to the first reduced-pressure delivery conduit 76.

Figure 6:
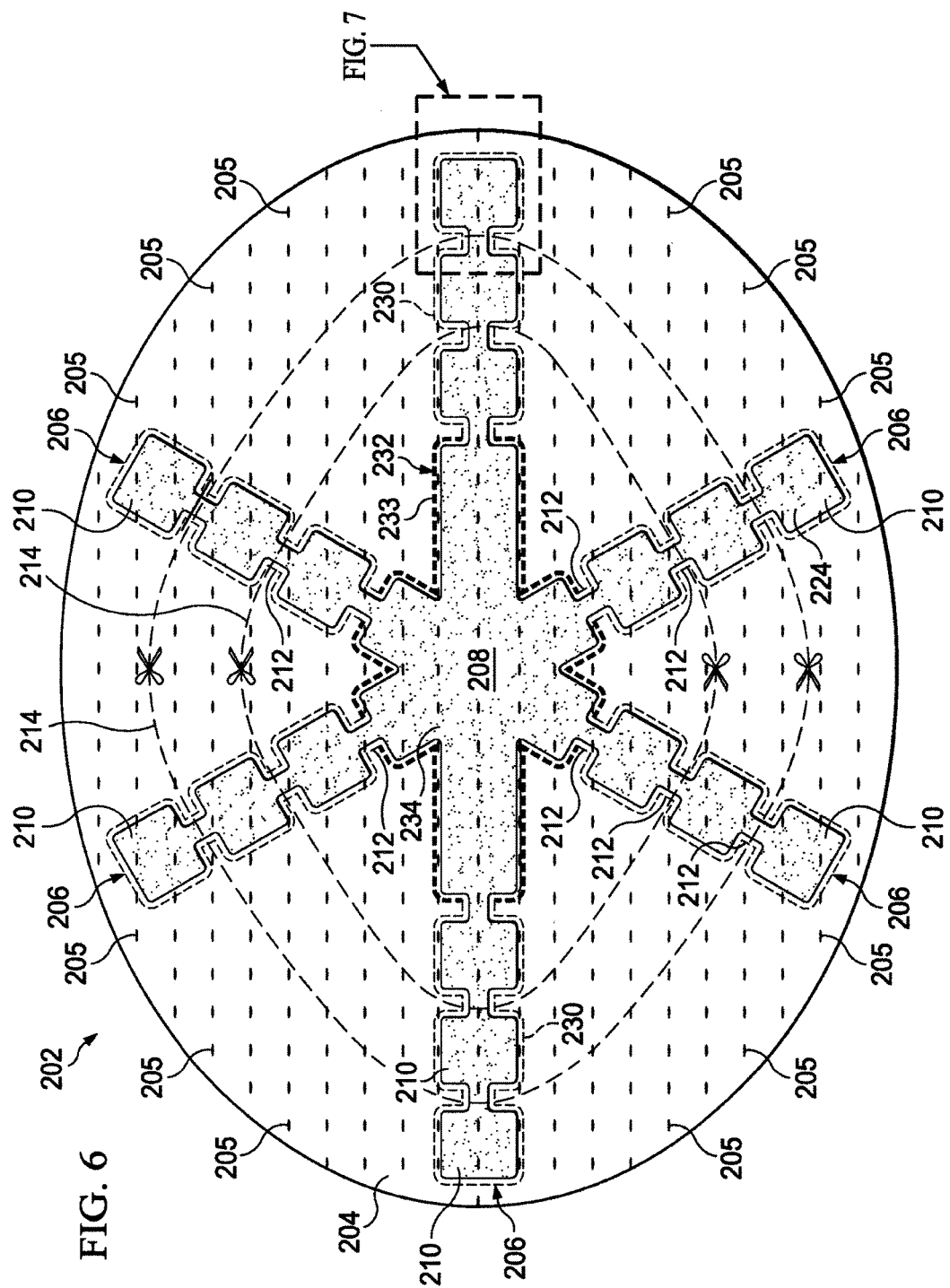
FIG. 6 is a schematic, plan view of an open-cavity, reduced-pressure treatment device according to another illustrative embodiment.
Figure 7:
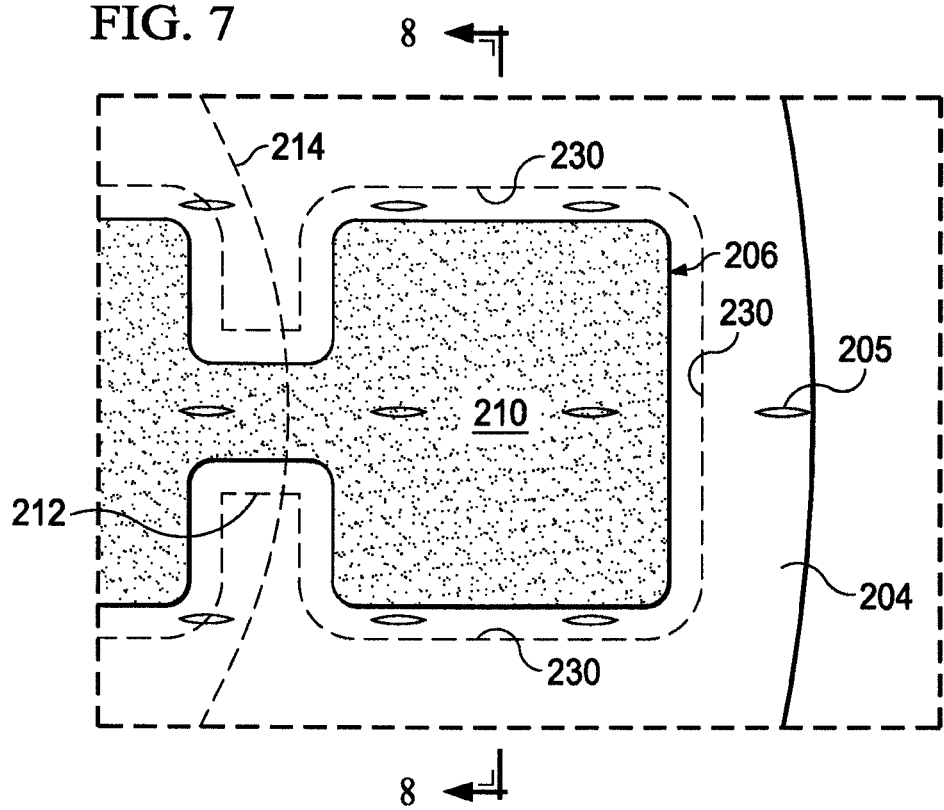
FIG. 7 is a schematic, plan view of a detail of the treatment device of FIG. 6.
Figure 8:
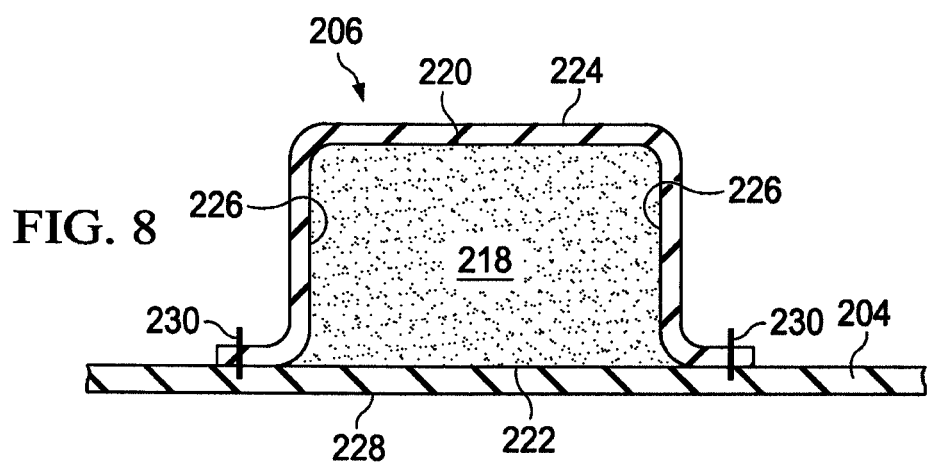
FIG. 8 is a schematic cross section of a portion of the treatment device of FIG. 7 taken along line 8-8.

Referring primarily now to FIGS. 6-8, another illustrative embodiment of an open-cavity treatment device 202, which might be used with the reduced-pressure, abdominal treatment system 30 of FIG. 1, is presented. The open-cavity treatment device 202 is analogous in most respects to the open-cavity treatment device 50 of FIGS. 1-5. The open-cavity treatment device 202 has a non-adherent drape 204, a plurality of encapsulated leg members 206, and a central connection member 208. In this illustrative embodiment, the non-adherent drape 204 is formed with an oval or arcuate shape, but various shapes are possible. The non-adherent drape 204 is formed with a plurality of fenestrations 205 therethrough. The non-adherent drape 204 also forms a second leg encapsulating member 228 and a second connection encapsulation member (not shown, but see by analogy 152 in FIG. 4), and the fenestrations 205 in the non-adherent drape 204 serve as flow channels for the encapsulated leg members 206 and the central connection member 208 on the second, inward-facing side.

Each of the plurality of encapsulated leg members 206 may be formed with a plurality of leg modules 210 with manipulation zones 212 between adjacent leg modules 210. The manipulation zones 212 facilitate maneuvering of the plurality of encapsulated leg members 206 within the abdominal cavity and provide an easier location at which to cut the encapsulated leg members 206 when the open-cavity treatment device 202 is being sized. In this regard, visual indicia 214 may be added on the non-adherent drape 204 to help the healthcare provider know where to cut the non-adherent drape 204 for different sizes of application within the abdominal cavity. The visual indicia 214 may include cut lines formed with biocompatible ink or welds or fenestrations or other markings that run, at least in part, through the manipulation zones 212. The visual indicia 214 may also show size graduations.

Referring now primarily to FIG. 8, a lateral cross section of the encapsulated leg member 206 is presented. The encapsulated leg members 206 are formed with a leg manifold member 218 having a first side 220 and a second, inward-facing side 222. A first leg encapsulating member 224 covers the first side 220 of the leg manifold member 218 and covers lateral edges 226 of the leg manifold member 218. The second, inward-facing side 222 of the leg manifold member 218 is covered by a second leg encapsulating member 228, which in this embodiment is a portion of the non-adherent drape 204. The first leg encapsulating member 224 is coupled to the second leg encapsulating member 228 by any means known in the art, e.g., welding (e.g., ultrasonic or RF welding), bonding, adhesives, cements, etc. In this illustration, the first leg encapsulating member 224 is coupled to the second leg encapsulating member 228 by a weld 230. The weld 230 may be formed on a perimeter portion of each leg module 210 or elsewhere.

The central connection member 208 is formed analogously to the central connection member 96 in FIG. 4. The first connection encapsulation member 234 and the second connection encapsulation member (not shown but analogous to second connection encapsulation member 152 in FIG. 4) are coupled along a peripheral edge 232 using a weld 233 or other coupling means, e.g., welding (e.g., ultrasonic or RF welding), bonding, adhesives, cements, etc. The peripheral edge 232 of the first encapsulation member 234 and the second encapsulation member are not coupled in a way that closes off fluid flow between the encapsulated leg members 206 and the central connection member 208; that is, a flow path for fluids to flow from the encapsulated leg members 206 into the central connection member 208 exists.

According to one illustrative approach to constructing the open-cavity treatment device 202, the non-adherent drape 204 that is formed with fenestrations 205 and that may have visual indicia 214 is placed on a substantially flat surface or otherwise presented on a plane. The leg manifold members 218 are placed onto the non-adherent drape 204. The central connection member 208 is placed on the non-adherent drape 204. Alternatively, the central connection member 208 may be formed as an integral member with the leg manifold members 218, and in that case, the central connection member 208 and the leg manifold members 218 would be placed simultaneously. The first connection encapsulation member 234 is placed on the central connection member 208, and the first leg encapsulating member 224 is placed on first side, or top (for the orientation shown in FIG. 6), of the leg manifold members 218. Then welds 230 and 233 are applied. Thus, the open-cavity treatment device 202 is formed.

In an alternative embodiment, a first non-adherent drape 204, which includes fenestrations 205, may have the leg manifold members 218 and the central connection member 208 placed on the first non-adherent drape 204. Then, a second non-adherent drape, which has fenestrations, is placed over the first non-adherent drape 204, the leg manifold members 218, and the central connection member 208. Then a plurality of welds (e.g., thermal or RF) are made, and the perimeter of the two non-adherent drapes may be welded. In addition, other points on the drape may be welded together. In another alternative, the two non-adherent drapes may initially not have fenestrations, and fenestrations may be added separately to the non-adherent drapes after assembly so that the fenestrations line up. The fenestrations may also be formed with an electrical member that cuts and seals simultaneously to form "button hole" fenestrations through the two non-adherent drapes at the locations where the leg manifold and the central connection member are absent.

Figure 9:
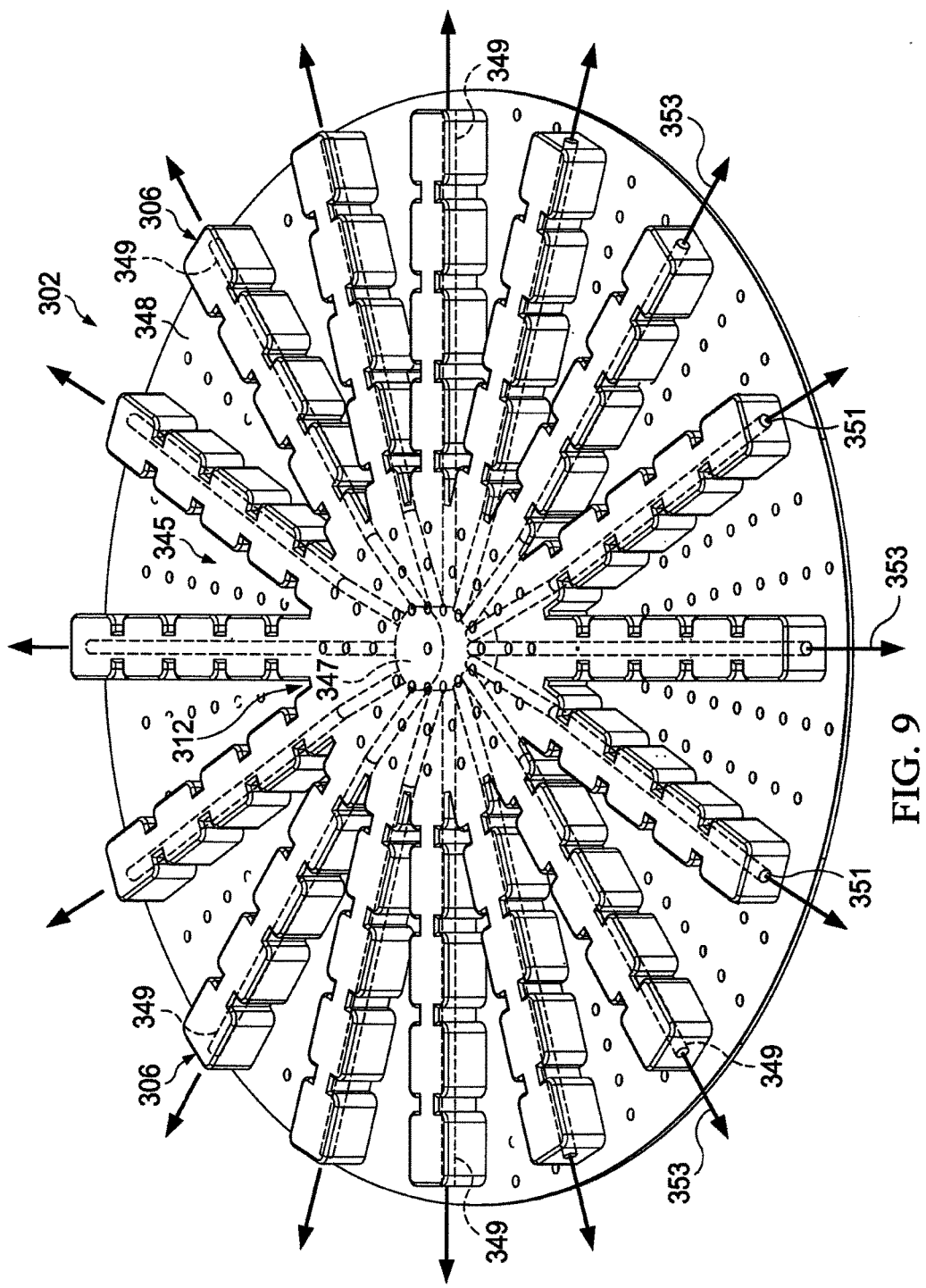
FIG. 9 is schematic, perspective view of another illustrative embodiment of an open-cavity, reduced-pressure treatment device.

Referring now to FIG. 9, another illustrative embodiment of an open-cavity treatment device 302 is presented. The open-cavity treatment device 302 is similar in most respects to that of the open-cavity treatment device 202 shown in FIG. 6. The open-cavity treatment device 302 has a plurality of encapsulated leg members 306 and a central connection member 312 on a non-adherent drape 348. The open-cavity treatment device 302 differs from the open-cavity treatment device 202 primarily in that a fluid delivery subsystem 345 has been added. The fluid delivery subsystem 345 allows various fluids, such as medicines or irrigation fluids, to be delivered into the abdominal cavity. The various fluids may then be removed by the action of the plurality of encapsulated leg members 306 and the open-cavity treatment device 302 itself. The fluid delivery subsystem 345 includes a central port member 347, which may be placed on or in the central connection member 312, for connecting to a delivery conduit (not shown) that delivers the fluid from a site external to the abdominal cavity to the central port member 347. Fluidly coupled to the central port member 347 is a plurality of fluid-delivery conduits 349. The fluid-delivery conduits 349 may run anywhere on the non-adherent drape 348. For example, the fluid-delivery conduits 349 may run along the sides of the encapsulated leg members 306 or on the opposite side of the non-adherent drape 348. In this illustrative embodiment, the fluid-delivery conduits 349 are shown running through the plurality of encapsulated leg members 306. The fluid-delivery conduits 349 are open on their distal ends 351 to allow the delivery of fluid there through. However, fluid delivery conduits 349 may have apertures at various locations for delivering fluid and may be closed at the distal ends 351 or open at the distal ends 351. The flow of fluid through the distal ends 351 of the fluid-delivery conduits 349 is suggested by arrows 353.

In use, the open-cavity treatment device 302 may be used in a fashion analogous to that of the open-cavity treatment devices 50 and 202, but at various times, it may be desirable to deliver a fluid through the fluid delivery subsystem 345. For example, it may be desirable to flush the abdominal cavity with an irrigation fluid or to deliver periodic doses of medicine.

Deep-Tissue Closure Subsystems and Devices

Referring to FIG. 1, the deep-tissue closure subsystem 56 of the reduced-pressure, abdominal treatment system 30 may be used for closing deep tissues, such as the fascia 36 and, in particular, to approximate the fascia edges 38. The deep-tissue closure subsystem 56, which includes the deep-tissue closure device 54, is shown. The deep-tissue closure subsystem 56 is particularly well suited for use within the abdominal cavity 32 that involves a deep tissue, such as in the fascia 36. The wound in the fascia 36 is shown with fascia edges 38 that typically define the deep-tissue wound. It is desirable to close or apply a closing force on the deep-tissue wound by proximating the fascia edges 38. As will be described in more detail, the deep-tissue closure device 54 helps with this purpose.

The deep-tissue closure device 54 may be placed on top of the open-cavity treatment device 50 and underneath the fascia 36. Referring primarily to FIGS. 1 and 10, the deep-tissue closure device 54 includes a contractible matrix 164, which has a first side 166 and a second, inward-facing side 168. The contractible matrix 164 is formed with a first plurality of apertures 170 through a contractible matrix material or structure. The contractible matrix 164 may also be formed so that a plurality of cells, e.g., open cells 172, is formed on the second, inward-facing side 168. The plurality of cells 172 may be formed with cell walls 174, which may include a second plurality of apertures 176. The first plurality of apertures 170 may be centered on the cells 172.

When reduced pressure is delivered to the contractible matrix 164, a gripping force is developed and an inward force. The reduced pressure acts through the first plurality of apertures 170 to provide a gripping force on the fascia 36. The gripping force holds, or grips, the fascia 36. The reduced pressure may be supplied to the fascia 36 from underneath (for the orientation shown) via fluid communication with the open-cavity treatment device 50, the cells 172, and the first plurality of apertures 170. Reduced pressure may additionally or alternatively be supplied via the manifold 64 and the second plurality of apertures 176. The gripping force on the fascia 36 is represented by arrows 178.

In addition to providing a gripping force through the apertures 170, the reduced pressure also urges the contractible matrix 164 inward, i.e., in the direction shown by arrows 29. "Inward" in this context means toward a center portion of the reduced-pressure, deep-tissue closure device 54. Alternatively, "inward" may be defined as in a direction that would pull the tissue, e.g., the fascia 36, towards the fascia edges 38 of the tissue wound for a deployed reduced-pressure, deep-tissue closure device 54. As the reduced pressure acts on the contractible matrix 164, the contractible matrix 164 grips the fascia 36 and goes from a non-contracted position to a contracted position. In one embodiment, the contractible matrix 164 includes cells that collapse laterally and thereby contract. The side walls, which are flexible, of the cells move closer to one another under the influence of reduced pressure. Because the reduced pressure on the first plurality of apertures 170 grips the fascia 36, and the reduced pressure also causes the contractible matrix 164 to contract, a closing force is developed and applied to the fascia 36 that urges the fascia edges 38 into closer approximation. Thus, the fascia 36 experiences a closing force and can be closed or urged into a closed position using reduced pressure.

In one embodiment, the contractible matrix 164 includes a plurality of cells, e.g., cells 172, that collectively define a first volume ($V_1$) when no reduced pressure is applied, e.g., at ambient pressure. When reduced pressure is applied to the cells, the cells collapse or otherwise move such that a second volume is defined ($V_2$). The second volume is less than the first volume ($V_1$), i.e., $V_1 > V_2$, and this change in volume is associated with contraction.

The deep-tissue closure subsystem 56 is able to provide a closing force on deep tissue, such as fascia 36, and to help provide reduced-pressure treatment within the abdominal cavity 32 and, in particular, to provide reduced-pressure treatment proximate the tissue site 34. The reduced pressure may be applied to the tissue site 34 and the abdominal cavity 32 to help promote removal of ascites, exudates or other liquids. The reduced pressure may be applied also to stimulate the growth of additional tissue.

In using the deep-tissue closure subsystem 56, a number of different embodiments of the deep-tissue closure device 54 may be used. Functionally, it is desirable for the deep-tissue closure device 54 to grip the deep tissue without puncturing the deep tissue and to pull the deep tissue towards the center, e.g., toward the center of a deep-tissue wound 165. When applied to the fascia 36, the deep-tissue closure device 54 approximates the fascia edges 38.

Figure 11:
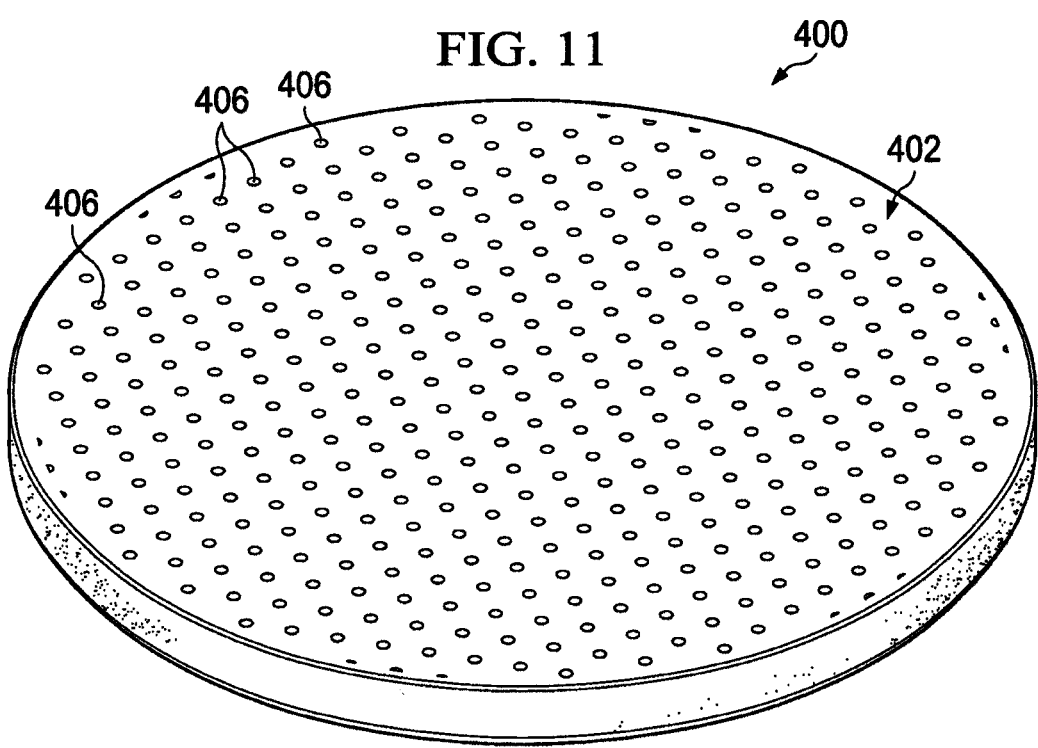
FIG. 11 is a schematic, perspective view, which shows a first side (top), of a contractible matrix according to one illustrative embodiment.
Figure 12:
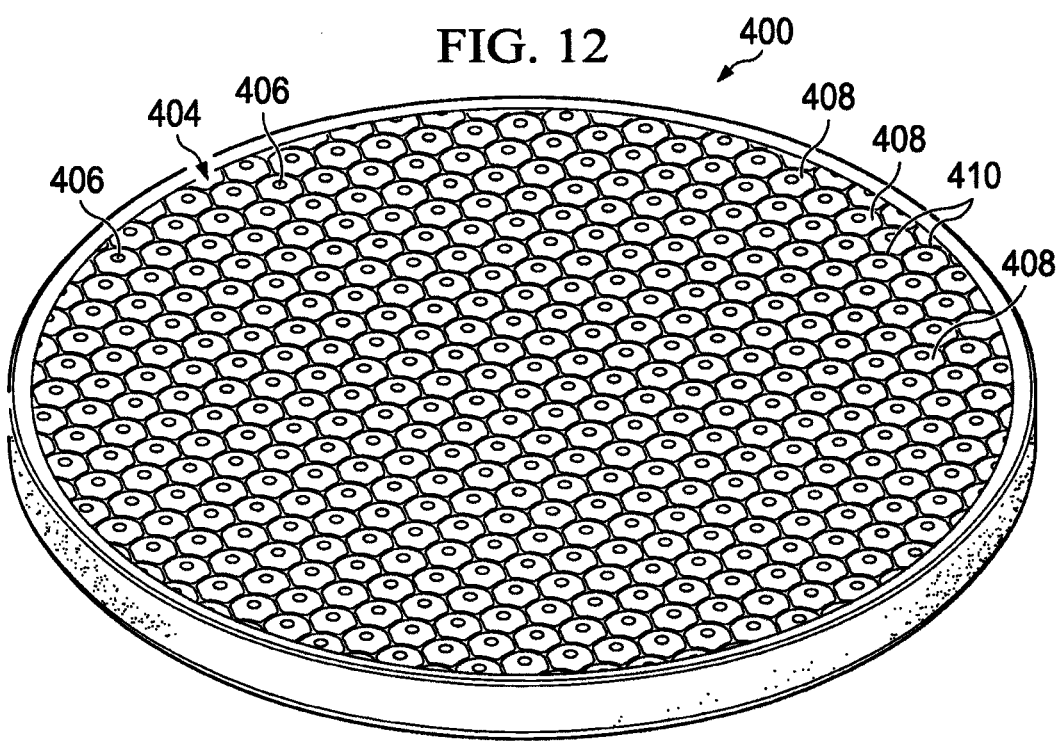
FIG. 12 is a schematic, perspective view, which shows a second (inward-facing) side, of the contractible matrix of FIG. 11.

Referring primarily now to FIGS. 11 and 12, a contractible matrix 400 for use as part of a reduced-pressure, deep-tissue subsystem is presented. The contractible matrix 400 has a first side 402 and a second, inward-facing side 404. FIG. 11 presents the first side 402, and FIG. 12 presents the second, inward-facing side 404. In this particular illustrative embodiment, the contractible matrix 400 is formed with a solid circular shape, but numerous other shapes, such as the elliptical shape shown in FIG. 13, an arcuate shape, a rectangular shape, an irregular shape, etc., may be used. The first side 402 of the contractible matrix 400 has a first plurality of apertures 406 formed there through and that extend to the second, inward-facing side 404. As shown in FIG. 12, a plurality of cells 408 is formed on the second, inward-facing side 404. The cells 408 each have an aperture 406 and an open cell portion. Each open cell 408 is formed with cell walls 410. Each cell wall 410 may have an intercellular aperture through the cell wall 410 to form a second plurality of apertures analogous to the second plurality of apertures 176 in FIG. 10. In this particular illustrative embodiment, the plurality of cells 408 may be formed as honeycomb cells centered around each of the first plurality of apertures 406. Other shapes for the cells 408 are possible as mentioned further below.

Figure 13:
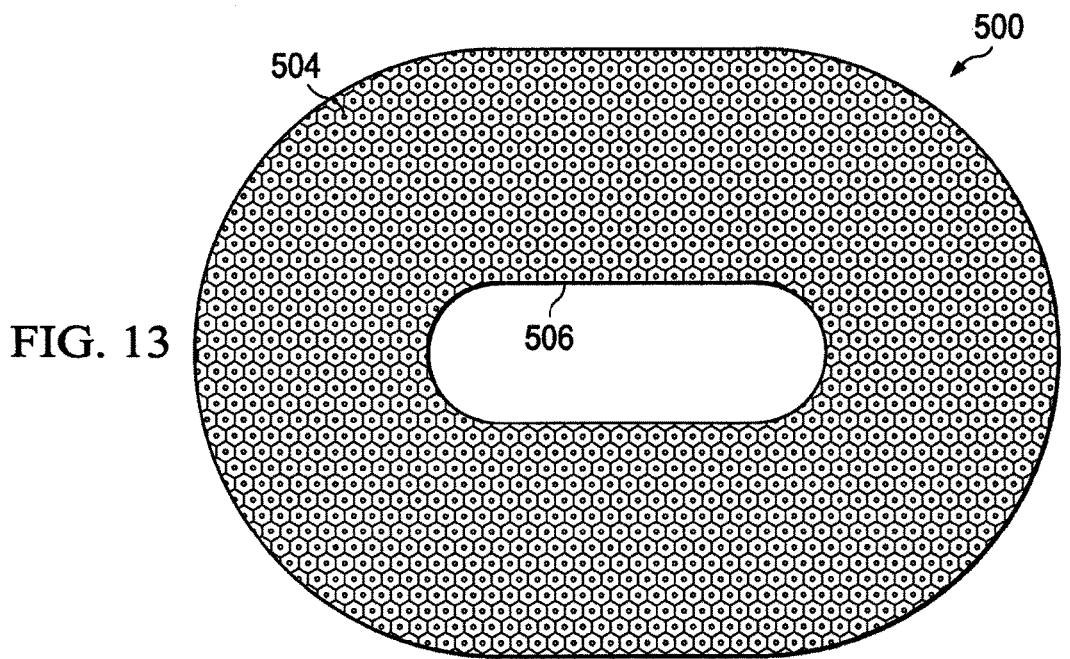
FIG. 13 is a schematic, top view of another illustrative embodiment of a contractible matrix.
Figure 14:
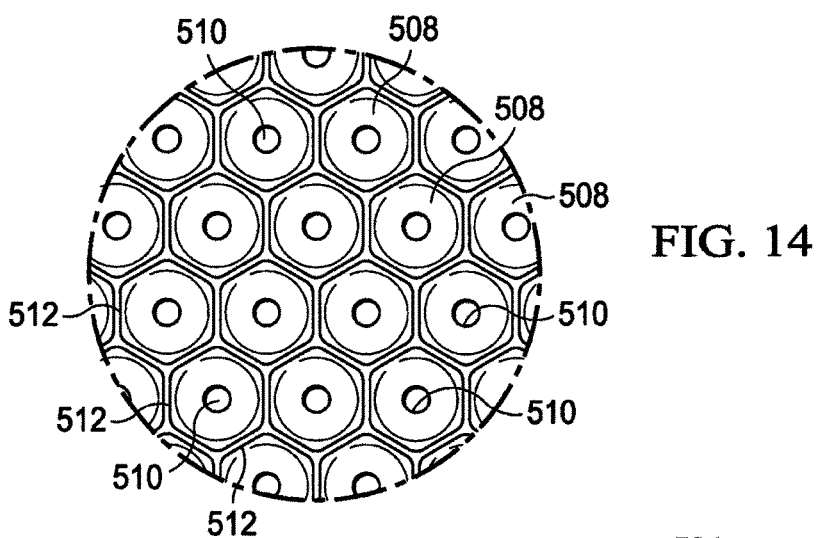
FIG. 14 is a detail of a portion of the contractible matrix of FIG. 13.

Referring now to FIGS. 13-14, another illustrative embodiment of a contractible matrix 500 is presented. The contractible matrix 500 has a first side and a second, inward-facing side 504. The contractible matrix 500 in this particular illustrative embodiment is formed with an oval shape that has a central opening 506, but as shown in FIG. 11 could be formed without such an opening. As shown in FIG. 14, the second, inward-facing side 504 of the contractible matrix 500 may be formed with a plurality of cells 508, each centered on a first plurality of apertures 510. The plurality of cells 508 may be formed by a plurality of interconnected cell walls 512. The cell walls might be formed with a second plurality of apertures formed through the cell wall analogous to the second plurality of apertures 176 in FIG. 10.

Figure 15:
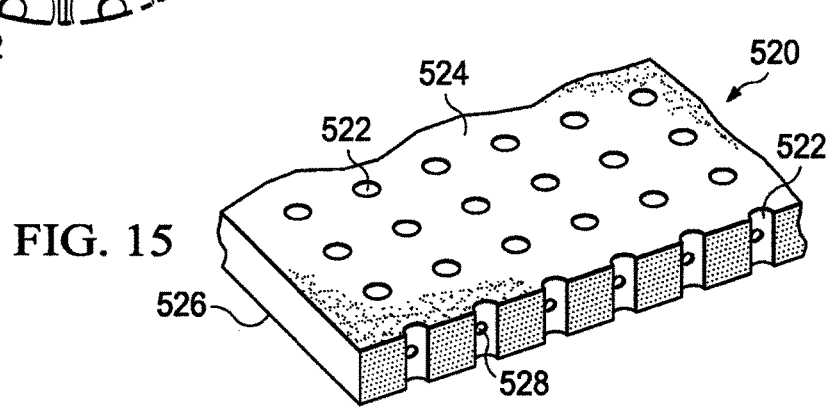
FIG. 15 is a schematic, perspective view of a portion of an illustrative embodiment of a contractible matrix.

Referring now to FIG. 15, another illustrative embodiment of a contractible matrix 520 is presented. The contractible matrix 520 may be used in the reduced-pressure, deep-tissue closure subsystem 56 of FIG. 1. The contractible matrix 520 in this illustrative embodiment is rectangular in shape and has a first plurality of apertures 522 that go from a first side 524 to a second, inward-facing side 526 of the contractible matrix 520. A second plurality of apertures 528 may connect the first plurality of apertures 522 or some portion thereof.

In an alternative embodiment, the contractible matrix 520 may have apertures 522 on the first side 524 but no corresponding aperture on the second, inward-facing side 526. Thus, the contractible matrix 400 has cells that open only to the first side 524 and may have apertures 528, which provide reduced pressure into the cells. When reduced pressure is supplied through apertures 528, the deep tissue is gripped by the apertures 522 and the side walls of the cells are pulled into closer proximity causing the contractible matrix 520 to contract.

A number of different substances might be used to form the contractible matrices, e.g., the contractible matrix 164 of FIG. 1, the contractible matrix 400 of FIGS. 11 and 12, the contractible matrix 500 of FIGS. 13 and 14, and the contractible matrix 520 of FIG. 15. Typically, a flexible, contractible material is used for the matrices. For example, these contractible matrices 164, 400, 500, and 520 may be formed from flexible, thermal plastic elastomers (TPE); thermoplastic urethane (TPU); silicone rubber; etc. Foam is not used for the contractible matrices. The material from which the contractible matrices are formed preferably avoid the ingrowth of any tissue. Moreover, a number of different cell geometries may be utilized in the contractible matrices. For example, the possible cell geometries include honeycomb, round-shaped, diamond-shaped, gear-shaped cells, etc. While foam is not used typically, in one embodiment, the contractible matrix could be formed from a sealed or encapsulated foam member that has apertures for gripping the tissue and a reduced-pressure supply interface.

In one illustrative embodiment, the contractible matrix may be formed with a TPU honeycomb material that includes honeycomb cells that are formed with fusion bonding. In another illustrative embodiment, the contractible matrix may be formed from a thermal plastic elastomer (TPE) that allows for expansion and contraction in the xy plane (the plane within the page for FIG. 13) while holding a fairly constant dimension in the z direction (coming out of the page on FIG. 13). In this embodiment, the contractible matrix may have a stronger material (or more material) concentrated in the z direction than in the xy directions. Alternatively or in addition, voids may be added to prescribe the pattern of collapse. Alternatively or in addition, strengthening members, e.g., filaments, may be added in the z direction to avoid collapse in that direction. In another illustrative embodiment, the contractible matrix may be formed using a thermoplastic urethane (TPU) material that may have an additional film on the contractible matrix on the first side, e.g., on first side 402 of the contractible matrix 400 of FIG. 11. These are only some illustrative examples.

Surface-Wound Closure Subsystems

Figure 16:
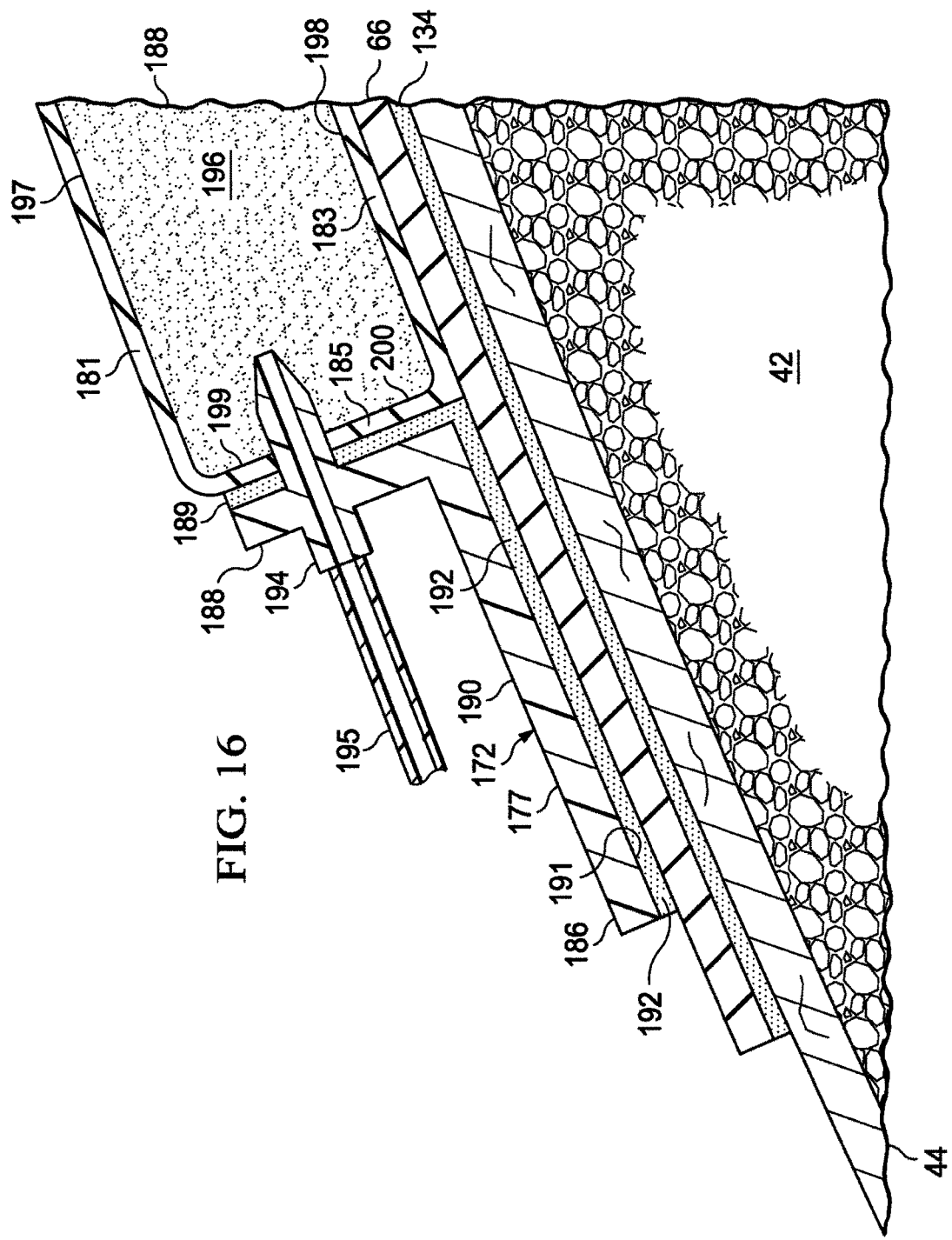
FIG. 16 is a schematic, cross-sectional view of a portion of the illustrative surface-wound closure subsystem of FIG. 1.

Referring again to FIG. 1, the surface-wound closure subsystem 60 is now presented. It is desirable to help provide a closing force to the surface wound 180 on the epidermis 44 and, in particular, between the surface-wound edges 182. As shown in FIGS. 1 and 16, the surface-wound closure subsystem 60 may be used for this purpose. The surface-wound closure subsystem 60 develops a closing force represented by arrows 184 that is communicated to the epidermis 44 and urges the surface-wound edges 182 towards each other. The surface-wound closure subsystem 60 may include a first attachment member 186 that has a first base member 177 and a first wall 188, or wall member, (FIG. 16). The sealed contracting member 196 may be secured to the wall 188 by a securing device, e.g., adhesive 189. The first base member 177 has a first side 190 and a second, inward-facing side 191. The first base member 177 and the first wall 188 may be made from numerous materials, but a material is preferred that provides some flexibility. For example, the first attachment member 186 may be formed with the first base member 177 and the first wall 188 made from polypropylene, or a rigid silicone, etc.

A first adhesive 192 may be applied to the second, inward-facing side 191 of the first base member 177 to allow the first base member 177 to be releasably attached directly to a portion of a patient's epidermis 44 or indirectly if a polyurethane film or other sealing member 66 is placed on the epidermis 44 first. In addition to the first adhesive 192, staples, or sutures, or other invasive approaches might be used to attach the first base member 177. The first attachment member 186 may be applied directly on top of the epidermis 44, or on top of the sealing member 66, so that whatever forces are applied on the first attachment member 186 are transmitted directly, or indirectly, to the epidermis 44. References to applying the first attachment member 186 to the epidermis 44 should be deemed to include application on top of the sealing member 66 as well.

Across the surface wound 180 from the first attachment member 186 is a second attachment member 193. The second attachment member 193 is analogous to the first attachment member 186. While the surface-wound closure subsystem 60 of FIG. 1 only shows two attachment members 186, 193, other attachment members may be dispersed around the surface wound 180 in a spaced fashion and typically in pairs. Having at least two attachment members, e.g., attachment members 186 and 193, allows the closing force to be developed.

One or more of the attachment members, e.g., attachment member 186, has a reduced-pressure interface 194 for receiving reduced pressure from a second reduced-pressure delivery conduit 195. For example, as shown in FIG. 16, the first attachment member 186 may include the reduced-pressure interface 194 to which the second reduced-pressure delivery conduit 195 is fluidly coupled.

The surface-wound closure subsystem 60 includes a sealed contracting member 196. The sealed contracting member 196 may be formed from the same type of materials as the manifold 64, but it may be desirable to include a material that has fewer apertures or holes through the material. The sealed contracting member 196 may be formed from a contracting manifold material that is enveloped by a first sealing member 181 and a second sealing member 183. In addition, it may be desirable in some situations to have a material that will contract less in the vertical (for the orientation shown in FIG. 1) and more in the horizontal plane (for the orientation shown FIG. 1). The sealed contracting member 196 has a first side 197 and a second, inward-facing side 198. The sealed contracting member 196 also has a peripheral edge 199.

The sealed contracting member 196 may be sealed by having the first sealing member 181 (FIG. 16) applied to the first side 197, and the second sealing member 183 applied to the second, inward-facing side 198. The peripheral edge 199 may be sealed by a peripheral sealing member 185 having a surface 200 disposed against the peripheral edge 199. The wall 188 may also be used to the seal peripheral edge 199. Similarly, the second, inward-facing side 198 may be sealed by placement against the sealing member 66 or the patient's epidermis 44. The sealed contracting member 196 might also be sealed by being coated with a gas-impervious material. The sealed contracting member 196 may be sealed using polyurethane film or silicone as the sealing members 181, 183 and then ultrasonically welding or RF welding the ends of the sealing members 181, 183 to cover the peripheral edge 199. When reduced pressure is supplied to the sealed contracting member 196, the sealed contracting member 196 contracts to develop the closing force, which is represented by the arrows 184.

The sealed contracting member 196 may be formed with an opening 187 (FIG. 1) on a portion of the sealed contracting member 196 for receiving an extension portion 179 of the reduced-pressure interface 72. The extension portion 179 extends through the sealed contracting member 196 and into the manifold 64.

There are many ways of developing the reduced pressure to be used with the surface-wound closure subsystem 60. In the illustrative embodiment shown, the reduced-pressure supply subsystem 62 (FIG. 1) may have a second reduced-pressure source 84 that delivers reduced pressure to the second reduced-pressure delivery conduit 195, which delivers the reduced pressure to the second reduced-pressure interface 194. As suggested by conduit 86 (shown in broken lines), the second reduced-pressure source 84 could be used to provide reduced pressure to the first reduced-pressure delivery conduit 76 (in addition to or in lieu of first reduced-pressure source 77) as well as to the second reduced-pressure delivery conduit 195. Alternatively, the first reduced-pressure source 77 could supply reduced pressure through conduit 86 to the second reduced-pressure conduit in addition to or in lieu of the second reduced-pressure source 84.

Referring now to FIG. 17A, a surface-wound closure device 600 for providing a closing force on a surface wound, e.g., surface wound 180 in FIG. 1, is presented. The surface-wound closure device 600 may be used as the surface-wound closure subsystem 60 of FIG. 1. The surface-wound closure device 600 has a plurality of attachment members: a first attachment member 602, a second attachment member 604, a third attachment member 606, and a fourth attachment member 608. Each attachment member 602, 604, 606, 608 has an attachment device for releasably attaching the member to the patient's epidermis (or to a sealing member). For example, the first attachment member 602 includes an attachment device that is an adhesive 610 for attachment to the patient's epidermis and similarly, third attachment member 606 has an adhesive 612. While not shown, the second and fourth attachment members also have an attachment device, such as an adhesive, for securing the members to a patient's epidermis. While non-invasive means are generally considered preferable, it may also be that the attachment members 602, 604, 606, 608 may be secured using sutures, staples, or other invasive mechanical devices.

A wall 614, which is coupled to the plurality of attachment members, forms a circumferential wall having an interior space into which a contracting member 616, or contracting material, is placed. The contracting member 616 is attached to the circumferential wall 614 at least at points proximate to each attachment member 602, 604, 606, 608. The circumferential wall 614 may be made of polypropylene, rigid silicone, or other semi-rigid material that allows the circumferential wall 614 to flex when in a closing mode, i.e., when reduced pressure is applied. The contracting member 616 may be made of the same kind of materials as sealed contracting member 196 in FIG. 1. The contracting member 616 in operation should be sealed and may be sealed by films, layers, or drapes being applied to a first side 618, or top side (for the orientation shown). The contracting member 616 may also be sealed with the circumferential wall 614 covering the peripheral edge, the sealing member may provide a seal on the bottom, and then a film or drape placed over the top. The contracting member 616 may simply be enveloped in a polyurethane film that has been welded to form an envelope around the material. An opening 620 may be formed through the contracting member 616. The opening 620 is for placement of part of a reduced-pressure interface, or port, extending to a manifold below the surface-wound closure device 600. A reduced-pressure conduit 622 delivers reduced pressure into the contracting member 616; this may be accomplished by directly applying the reduced-pressure conduit 622 into any portion of the contracting member 616, but is shown using a reduced-pressure interface 624 formed on a portion of the circumferential wall 614.

In operation, the attachment members, e.g., first attachment member 602 and second attachment member 604, are placed opposite each other and on each side of a surface wound and releasably attached. Thus, for example, the first attachment member 602 and the fourth attachment member 608 may be releasably secured to one side of a surface wound at different spaced portions and the attachment members 604 and 606 may be placed on the other side of the surface wound. As the surface-wound closure device 600 is installed, the surface-wound closure device 600 is in a non-contracted position.

Once the surface-wound closure device 600 is installed on the surface wound, reduced pressure is supplied to the reduced-pressure conduit 622. The contracting member 616 contracts under the supplied reduced pressure causing at least portions of the circumferential wall 614 to be pulled towards a central portion, and in turn, to develop the forces transmitted to the attachment members which pull towards each other. Thus, a net closing force is developed and transmitted to the epidermis through the attachment members 602, 604, 606, and 608. FIG. 17B shows the surface-wound closure device 600 in a top view and in a non-contracted position, and FIG. 17C shows the surface-wound closure device 600 in the contracted position.

Figure 18:
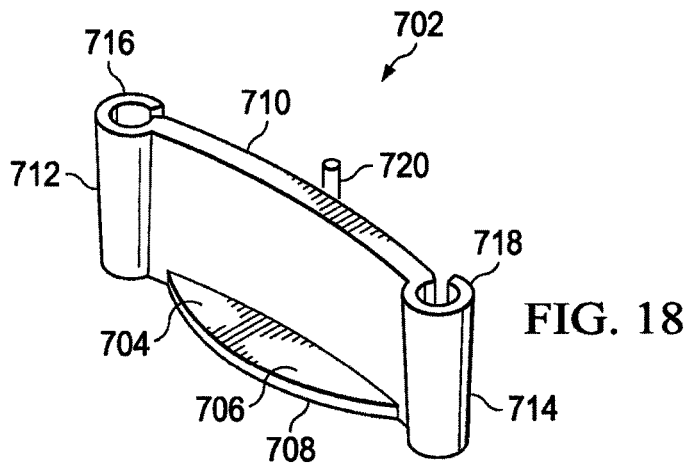
FIG. 18 is a schematic, perspective view of an illustrative embodiment of an attachment-base member for use as part of an illustrative embodiment of a surface-wound closure subsystem.

Referring now to FIGS. 18 to 21B, a modular, reduced-pressure wound-closure system 700, which is suitable as another illustrative embodiment of a surface-wound closure subsystem 60, is presented. The modular, reduced-pressure wound-closure system 700 uses a number of modular components that may be movably coupled to accommodate various sizes and shapes of wounds and to provide a closing force directed toward a central portion of the surface wound. Referring initially to FIG. 18, a plurality of attachment-base members, such as attachment-base member 702, may be used. The attachment-base member 702 has a base 704, which has a first side 706 and a second, inward-facing side 708. The second, inward-facing side 708 of the base 704 may have an adhesive (not shown but analogous to 610 in FIG. 17A) for attaching the attachment-base member 702 to a patient's epidermis (or to a sealing member). The adhesive on the second, inward-facing side 708 may be initially covered with a releasable backing material that may be removed before application on the patient. The attachment-base member 702 also includes a wall 710 that is coupled to the base 704 or formed integrally with the base 704. The wall 710 has a first end 712 and a second end 714. The first end 712 may be formed with a first movable connection member 716 that is formed as an integral part or attached to the first end 712. The second end 714 may be formed with a second movable connection member 718. The wall 710 or base 704 may have a hook member 720 attached to the wall 710 or base 704. The hook member 720 may be used to help grip and hold a sealed contracting member 722 (see FIG. 21A).

Figure 19:
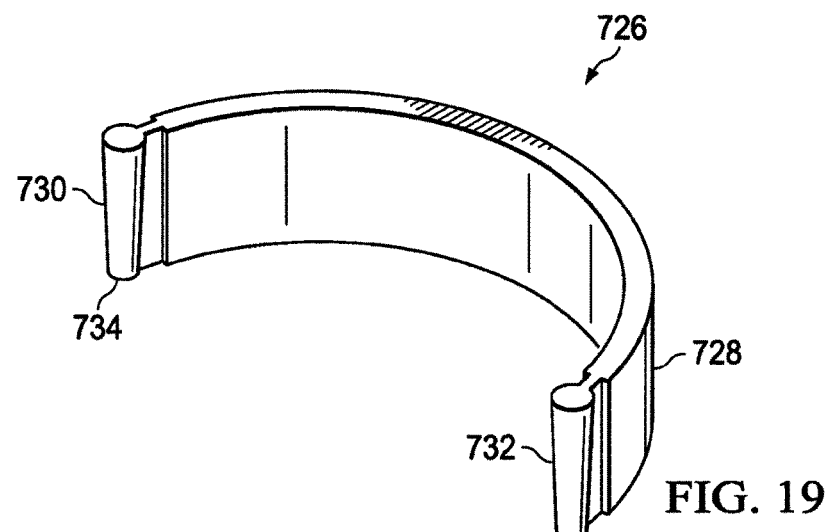
FIG. 19 is a schematic, perspective view of an illustrative embodiment of a connection member for use as part of an illustrative embodiment of a surface-wound closure subsystem.

Referring now to FIG. 19, a plurality of connecting members, such as connecting member 726, may be used as part of the modular, reduced-pressure wound-closure system 700. Each connecting member 726 has a second wall 728 with a first end 730 and a second end 732. The second wall 728 may be shaped to have an arcuate configuration as shown or may be straight. The first end 730 may be formed with, or have coupled to the first end 730, a third movable connection member 734. Similarly, the second end 732 may have a fourth movable connection member 736. The movable connection members 734 and 736 are sized and configured to cooperate with movable connection members, e.g., movable connection members 716 and 718, in a coordinated fashion that allows relative movement, such as pivotable movement, between each attachment-base member 702 and each adjacent, coupled connecting member 726. In this particular illustrative embodiment, the movable connection members 734 and 736 are shown as being pin-shaped members. The first and second movable connection members 716 and 718 are sockets that are sized and configured to receive the pin shapes of movable connection members 734 and 736.

Figure 20:
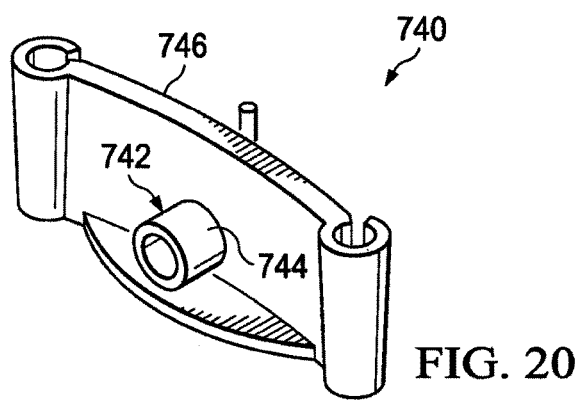
FIG. 20 is a schematic, perspective view of an illustrative embodiment of a reduced-pressure interface member for use as part of an illustrative embodiment of a surface-wound closure subsystem.

While a reduced-pressure conduit, such as conduit 622 in FIG. 17A, might be applied directly into the attachment-base member 702 through the wall 710, a reduced-pressure interface might be used on the wall 710 of the attachment-base member 702. Thus, for example, the attachment-base member 702 might be modified to form a reduced-pressure interface member 740 as shown in FIG. 20. The reduced-pressure interface member 740 is analogous to that of the attachment-base member 702 except that a reduced-pressure interface 742 has been included. The reduced-pressure interface 742 may be a port 744 that extends through a wall 746.

Figure 21A:
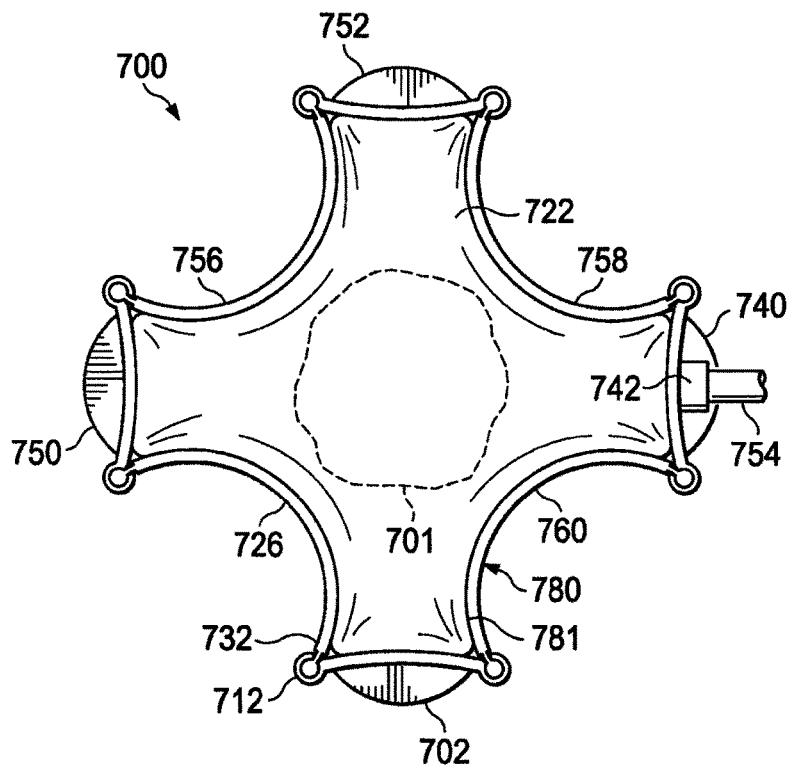
FIGS. 21A and 21B are schematic, plan views of an illustrative embodiment of a reduced-pressure, surface-wound closure subsystem shown in a non-contracted position (FIG. 21A) and a contracted position (FIG. 21B)
Figure 21B:
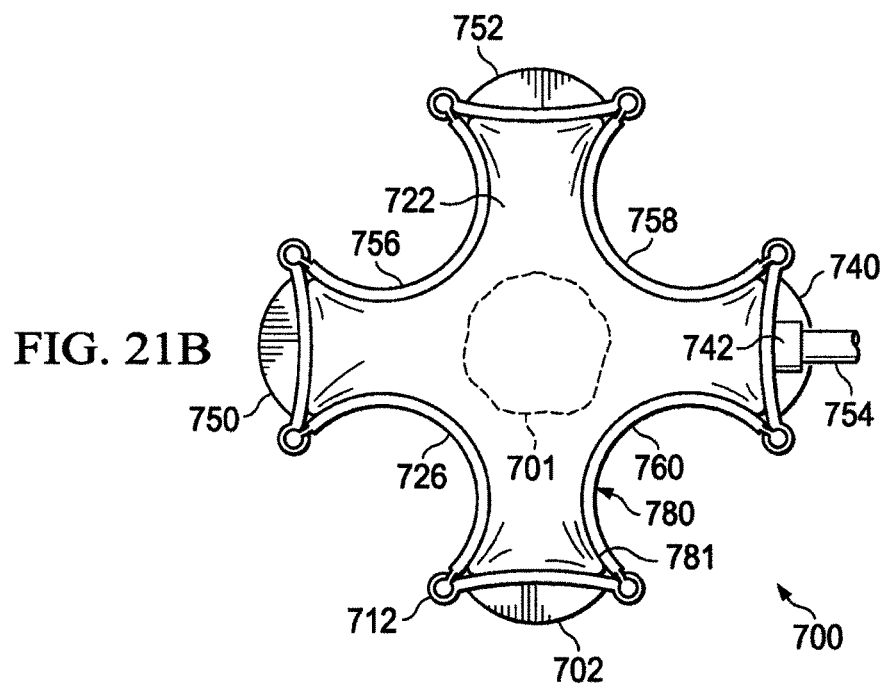

The previously presented modular components, attachment-base member 702, connecting member 726, and reduced-pressure interface member 740, may be combined to form various shapes; one example is shown in FIGS. 21A and 21B with the modular, reduced-pressure wound-closure system 700 shown around and over a surface wound 701. With reference primarily to FIG. 21A, the modular, reduced-pressure wound-closure system 700 is shown with a plurality of attachment-base members. In this instance, the modular, reduced-pressure wound-closure system 700 includes the first attachment-base member 702, a second attachment-base member 750, and a third attachment-base member 752. A fourth attachment-base member is shown, but has been modified to form the reduced-pressure interface member 740, which has the reduced-pressure interface 742. A reduced-pressure conduit 754 may be coupled to the reduced-pressure interface 742.

A plurality of movable connecting members is used to connect each of the plurality of attachment-base members 702, 750, 752, 740 (interface). Thus, in this illustrative embodiment, the attachment-base member 702 is movably coupled at the first end 712 to the first connecting member 726 at the second end 732 of the first connecting member 726. Similarly, the second attachment-base member 750 is movably coupled to the second connecting member 756. The second connecting member 756 is also movably coupled to the third attachment-base member 752. At the same time, the third attachment-base member 752 is movably coupled to a third connecting member 758, which is also movably coupled to the reduced-pressure interface member 740. The reduced-pressure interface member 740 is also movably coupled to a fourth connecting member 760. In this way the plurality of attachment-base members and plurality of connecting members form a circumferential wall 780 defining an interior space 781 into which sealed contracting member 722 is disposed.

It will be appreciated that the alternating members of the plurality of attachment-base members and plurality of connecting members provide for connections that move and are thus movably coupled. Movably coupling the members is helpful when the modular, reduced-pressure wound-closure system 700 goes from the non-contracted position of FIG. 21A to the contracted position shown in FIG. 21B. It will also be appreciated that while only four connecting members and four attachment-base members are shown in this illustration, any number of these components might be used for bigger or smaller applications. For example, a modular, reduced-pressure closure system 800 in FIG. 22 shows a much larger system configuration.

The modular, reduced-pressure closure system 800 in this illustrative embodiment includes a plurality of attachment-base members having seven attachment-base members 802 and another that has been modified to form a reduced-pressure interface 804. The modular, reduced-pressure closure system 800 also includes a plurality of connecting members, which in this illustrative embodiment includes eight connecting members 806. The plurality of attachment-base members 802 and the plurality of connecting members 806 are movably coupled to form a circumferential wall 808 that defines an interior space 810. A sealed contracting member 812 is placed within the interior space 810 and is coupled to at least the plurality of attachment-base members 802. When reduced pressure is supplied through a reduced-pressure interface 814 on the reduced-pressure interface 804, the reduced pressure causes the sealed contracting member 812 to contract and pulls each of the plurality of attachment-base members 802 toward a central portion. Thus providing a closing force.

Referring now to FIGS. 23A and 23B, one illustrative embodiment of a reduced-pressure connector 900 is presented. The reduced-pressure connector 900 is operable to fluidly connect two different compartments or areas. In the illustrative embodiment of FIGS. 23A and 23B, the reduced-pressure connector 900 has a first end 902 and a second end 904. An entry portion 906 is formed on the second end 904. The entry portion 906 may be shaped as an inverted conical section to facilitate insertion through various materials, such as sealing members and manifolds. On the first end 902, a plurality of flutes 908 may be located to facilitate fluid flow. A flange portion 910 may be formed between the first end 902 and the second end 904. The flange portion 910 has a first surface 912 and a second surface 914. In an alternative embodiment, the first end 902 may also be shaped and configured for easy entry through a sealing member or other material. Two different, illustrative applications of the reduced-pressure connector 900 are shown in FIGS. 24A and 24B.

Referring to FIG. 24A, a portion of a reduced-pressure, wound-closure and treatment system 1000 is presented. The reduced-pressure, wound-closure and treatment system 1000 is analogous in many respects to the surface-wound closure subsystem 60 of FIG. 1. A manifold 1018 is placed within a body cavity, e.g., an abdominal cavity 1010, to help provide reduced-pressure treatment therein. The manifold 1018 is shown proximate to subdermal tissue 1014 and a surface wound 1011.

A sealing member 1032 is placed on the patient's epidermis 1008 over the abdominal cavity 1010 and the surface wound 1011. The surface wound has wound edges 1012. The sealing member 1032 has an adhesive 1034 that helps to form a pneumatic seal with the epidermis 1008. The sealing member 1032 as applied forms a pneumatic seal over the abdominal cavity 1010.

A portion 1071 of a wound-closure device or subsystem is also presented. The portion 1071 includes a portion of a sealed contracting member 1088. The sealed contracting member 1088 is sealed, at least in part, by a first sealing member 1096 and a second sealing member 1098. The sealed contracting member 1088 is attached, at least at certain portions, to the patient's epidermis 1008. When reduced pressure is supplied to an interior of the sealed contracting member 1088, the sealed contracting member 1088 contracts and thereby pulls towards a central portion and develops a closing force that is transmitted to the surface wound 1011.

In the illustrative embodiments of FIGS. 24A and 24B, reduced pressure is supplied by a reduced-pressure source to a reduced-pressure conduit 1042. The reduced-pressure conduit 1042 is fluidly coupled to a reduced-pressure interface 1038, which has an extension portion 1102. In the embodiment of FIG. 24A, the extension portion 1102 extends through the sealing member 1032 and into the manifold 1018. Thus, reduced pressure is delivered to the manifold 1018 and pulls fluids towards the extension portion 1102 as suggested by arrows 1044. In this embodiment, the reduced-pressure connector 900 has been added. The reduced-pressure connector 900 is deployed with the first end 902 within the interior of the sealed contracting member 1088 and the second end 904 within the manifold 1018. The reduced-pressure connector 900 thereby fluidly couples the interior of the sealed contracting member 1088 with the manifold 1018. Reduced pressure is thereby delivered from the reduced-pressure interface 1038, to the manifold 1018, and to the interior of the sealed contracting member 1088. The reduced pressure delivered through the reduced-pressure connector 900 pulls fluids within the sealed contracting member 1088 as suggested by arrows 1045.

The first surface 912 of the reduced-pressure connector 900 abuts the sealing member 1032 and the second surface 914 abuts the manifold 1018. The reduced-pressure connector 900 may be deployed in numerous ways. For example, with reference to FIG. 17A, the reduced-pressure connector 900 can be placed over a cell, e.g., cell 625, of the contracting member 616, and pushed through the sealing member thereon. The entry portion 906 is shaped to facilitate such an entry. The sealing member thereon should self-seal after insertion, but an additional portion of sealing material could also be added over the insertion point. During insertion, the reduced-pressure connector 900 is pushed into the sealed contracting member 616 until the second surface 914 abuts the second (bottom for orientation shown) sealing member 1098 and the entry portion 906 extends out of the contracting member 616. Referring now primarily to FIG. 24A, in a like fashion, the entry portion 906 can then be inserted through the sealing member 1032 and into the manifold 1018. As noted earlier, numerous approaches may be taken for deploying the reduced-pressure connector 900 and the reduced-pressure connector 900 may take many different configurations, but the deployed reduced-pressure connector 900 functionally provides a fluid coupling of the sealed contracting member 1088 and the manifold 1018.

Referring now to FIG. 24B, another alternative is shown. In the embodiment of FIG. 24B, the extension portion 1102 of the reduced-pressure interface 1038 terminates within the sealed contracting member 1088 and delivers reduced pressure within the sealed contracting member 1088. The reduced-pressure connector 900 is deployed in the same manner as previously presented, but now delivers reduced pressure to the manifold 1018. In other words, fluids are drawn through the manifold 1018, through the reduced-pressure connector 900, through an interior of the sealed contracting member 1088 to the extension portion 1102 of the reduced-pressure interface 1038 and then through the reduced-pressure conduit 1042.

Figure 25:
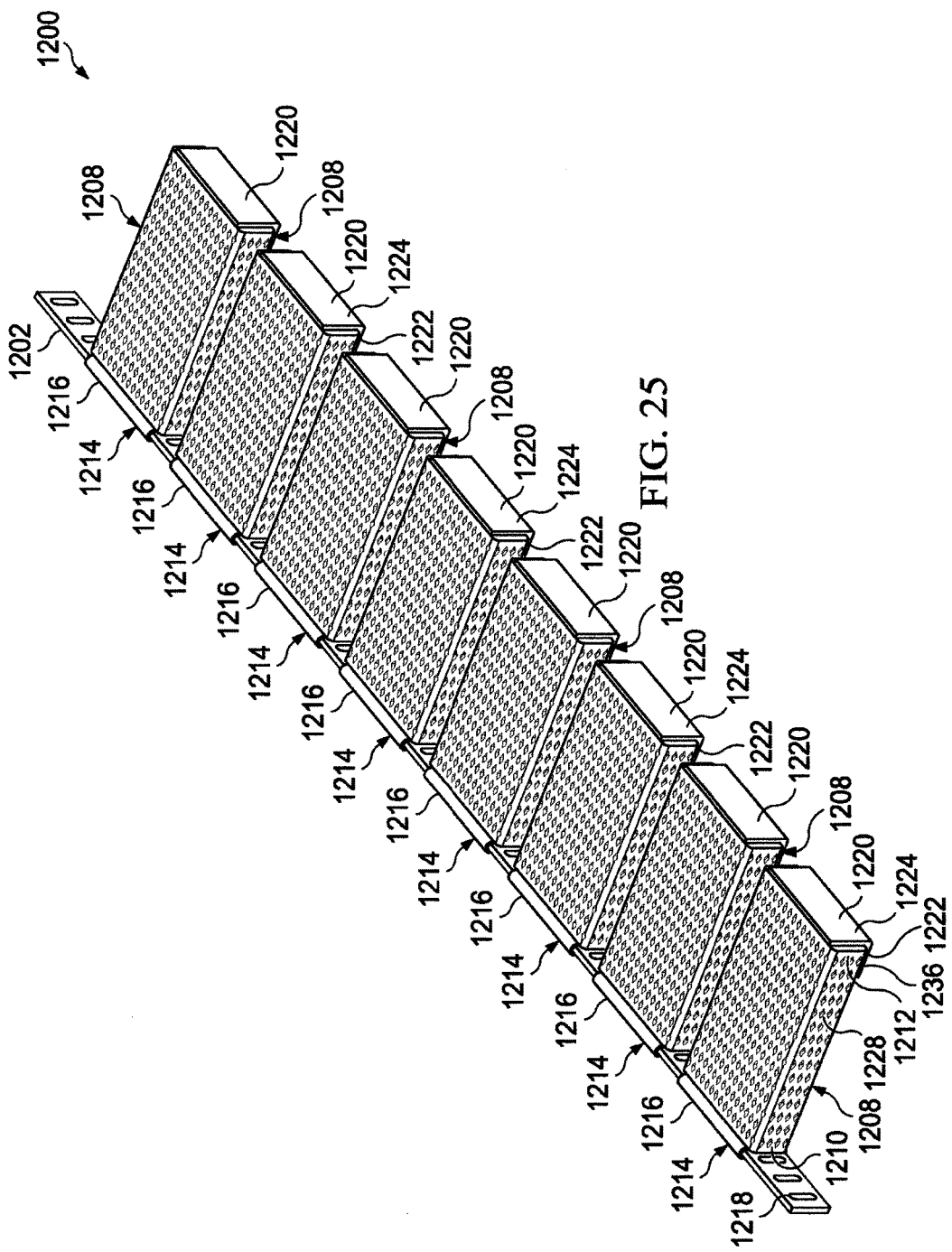
FIG. 25 is a schematic, perspective view of an illustrative embodiment of a portion of a reduced-pressure, surface-wound closure subsystem showing, amongst other things, an illustrative embodiment of a plurality of modular closing members.
Figure 26:
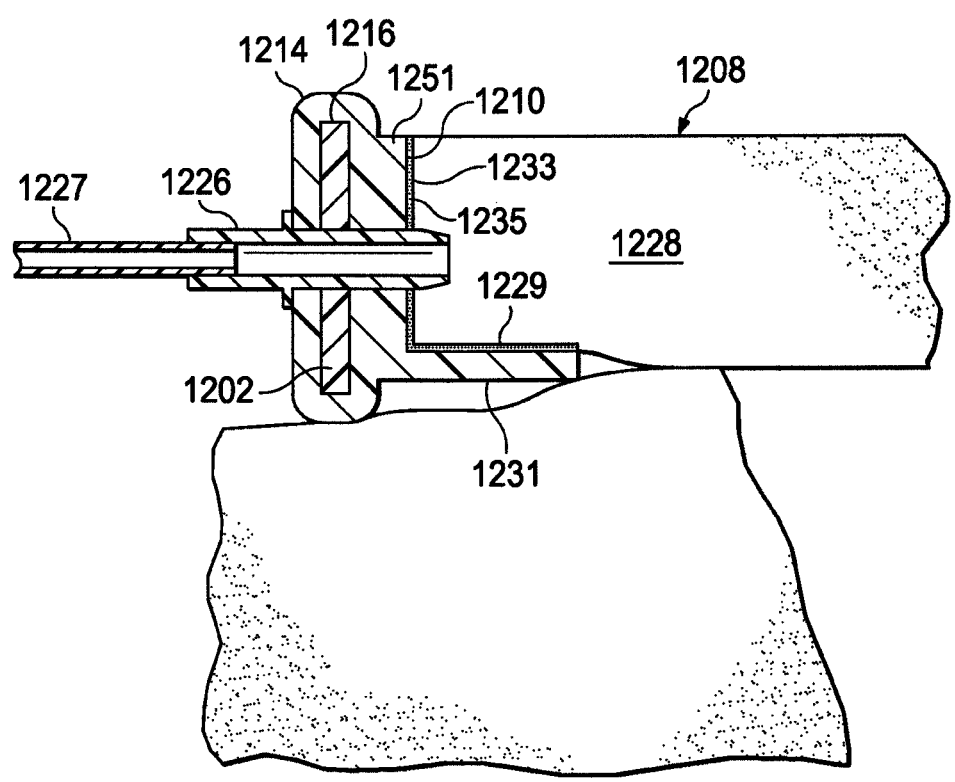
FIG. 26 is a schematic, cross-section of a portion of a modular closing member of FIG. 25.
Figure 27:
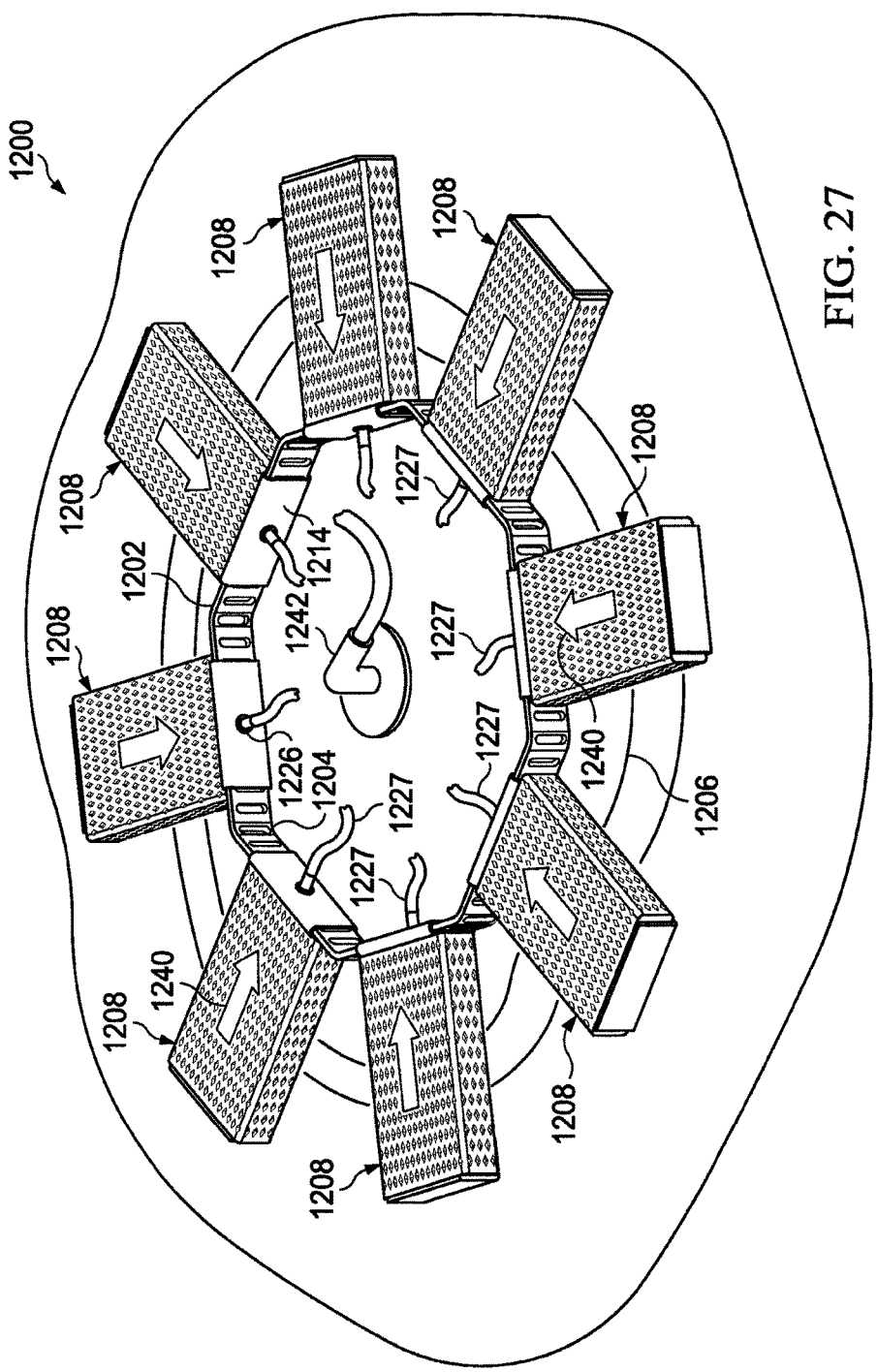
FIG. 27 is a schematic, perspective view of the illustrative wound-closure subsystem of FIGS. 25-26 shown applied over a surface wound of a patient.

Referring now to FIGS. 25-27, another illustrative embodiment of a modular, reduced-pressure closure system 1200, which is suitable as another illustrative embodiment of the surface-wound closure subsystem 60, is presented. The modular, reduced-pressure closure system 1200 includes a spacing member, e.g., a flexible strap 1202, which is shown in a linear position in FIG. 25 and shaped into a closed loop 1204 in FIG. 27. The flexible strap 1202 may be shaped into the closed loop 1204 around a surface wound 1206, such as an opening on a patient's abdomen. A plurality of modular closing members 1208 is selectively coupled to the flexible strap 1202. The number of modular closing members 1208 included in the plurality of modular closing members on the flexible strap 1202 is determined by the size of the closed loop 1204 needed to surround the surface wound 1206. Thus, to cover the surface wound 1206 in FIG. 27, eight modular closing members 1208 have been included on the flexible strap 1202. While a flexible strap 1202 has been referenced, any spacing member that holds the modular closing members 1208 in a spaced relationship around the surface wound 1206 may be used. For example, the spacing member may be one or more tie wires that hold the modular closing members 1208 in a spaced relationship or a flexible adhesive film placed on top of the modular closing members 1208 that hold the modular closing members 1208 in a spaced relationship.

Referring again primarily to FIG. 25, each of the modular closing members 1208 has a first end 1210 and a second end 1212. A connection member 1214 is coupled to the first end 1210 of each modular closing member 1208. In the illustrative embodiment of FIG. 25, each connection member 1214 includes an attachment loop 1216 through which the flexible strap 1202 may be placed. The attachment loops 1216 allow each modular closing member 1208 to be positioned in a desired location along the flexible strap 1202. A portion of each attachment loop 1216 may interface with one of a plurality of strap openings 1218 to help hold the connection member 1214 in a desired position on the flexible strap 1202.

Referring now primarily to FIG. 26, the second reduced-pressure interface 1226 is shown coupled to the connection member 1214. A reduced-pressure conduit 1227 is fluidly coupled to the second reduced-pressure interface 1226 in order to provide reduced pressure to the second reduced-pressure interface 1226. The second reduced-pressure interface 1226 delivers the reduced pressure to a sealed contracting member 1228 and may function as a pin to hold the connection member 1214 in place relative to the flexible strap 1202. The second reduced-pressure interface 1226 may extend through an opening in connection member 1214, through the attachment loop 1216, through the flexible strap 1202 and into the sealed contracting member 1228. In FIG. 26, one may see that the sealed contracting member 1228 may be held to a base 1231 by an adhesive layer 1229. Similarly, a peripheral edge 1233 of the sealed contracting member 1228 may be held to a wall 1251 of connection member 1214 by an adhesive layer 1235. In this way, reduced pressure can be supplied to the modular closing member 1208 and more particularly to the sealed contracting member 1228. FIGS. 28 and 29 show alternative ways of providing reduced pressure to the sealed contracting member 1228 as will be described further below.

The sealed contracting member 1228 is made of the same or similar materials as contracting member 196 (FIG. 1), 616 (FIG. 17A), and 722 (FIG. 21A). The sealed contracting member 1228 is sealed to form a pneumatic seal about the sealed contracting member 1228. An adhesive layer 1229 may be used to hold the sealed contracting member 1228 to the base 1231. An adhesive layer 1235 may be also be used to attach the peripheral edge 1233 of the sealed contracting member 1228 to the wall 1251.

At the other end of modular closing member 1208, attachment members 1220 may be coupled to each of the second ends 1212 of the modular closing members 1208. Referring again primarily to FIG. 25, each of the attachment members 1220 may be formed with a base 1222 and a wall 1224. An adhesive layer may be used to hold the sealed contracting member 1228 to the base 1222. An adhesive layer may also be used to hold the sealed contracting member to the wall 1224. An adhesive may be used to hold the inward-facing side 1236 of the base 1222 against the patient's epidermis.

Referring now primarily to FIG. 28, an alternative reduced-pressure interface 1327, which may be used as part of the modular, reduced-pressure closure system 1200, is presented. Reduced pressure may be provided to a sealed contracting member 1308 through the connection member. For example, the modular closing member may have a connection member 1316 that selectively attaches to a flexible strap 1302. An adhesive 1330 may be used to hold the sealed contracting member 1308 to the connection member 1316. The connection member 1316 may have a wall 1324 and a base 1322. A reduced-pressure interface 1327 may be formed on the base 1322 and configured to enter the sealed contracting member 1308. The reduced-pressure interface 1327 is sized and configured to engage a manifold 1380, which is in fluid communication, or is fluidly coupled, to a reduced-pressure source. The reduced pressure is delivered to the manifold 1380.

Referring now to FIG. 29, an attachment member 1420, which has a base portion 1422 and a wall 1424, is shown with an alternative reduced-pressure interface 1426. The reduced-pressure interface 1426 is formed through the wall 1424. A reduced-pressure conduit 1427 delivers reduced pressure from a reduced-pressure source to the reduced-pressure interface 1426. The reduced-pressure interface 1426 delivers reduced pressure to a sealed contracting member 1428. The sealed contracting member 1428 may be held to the base 1422 by an attachment device, e.g., adhesive 1430. The base 1422 may be held by an attachment device 1432, e.g., adhesive 1436, to the patient's epidermis. The sealed contracting member 1428 may also be held by an attachment device 1432, e.g., adhesive 1434, to the wall 1424.

With reference again to FIG. 27, in operation, the modular, reduced-pressure closure system 1200 is used by the healthcare provider who first assesses the size of the surface wound 1206 and determines the number of modular closing members 1208 that are appropriate for the size of the wound. A lookup table might be provided to suggest the number based on the linear measurement of the circumference of the surface wound 1206. An appropriate number, which make up the desired plurality of modular closing members 1208, are then selectively coupled to the flexible strap 1202. The flexible strap 1202 is shaped into the closed loop 1204 around the surface wound 1206 and is preferably disposed inboard of the peripheral edges of the surface wound 1206. The closed loop 1204 is secured as a loop using any number of means, such as a ratchet, snap, a fastener on the flexible strap 1202, ratchet ties, flexible peg and slot members, etc. Then, each of the plurality of attachment members 1220 are attached to the patient's epidermis proximate the edge of the surface wound 1206. As before, the statement that each of the plurality of attachment members 1220 are attached to the epidermis may include that the attachment member 1220 is attached on top of a sealing member being used for reduced-pressure treatment. When reduced pressure is supplied through the reduced-pressure conduit 1227 to the reduced-pressure interface 1226 of each modular closing member 1208, a closing force is developed as represented by arrows 1240.

The closed loop 1204 provides an open area in the middle of the loop which readily accommodates a reduced-pressure interface 1242 that may be used to supply reduced pressure to a portion of a reduced-pressure treatment system (see, e.g., subsystem 58 in FIG. 1).

General Operation

Referring primarily to FIG. 1, according to one illustrative approach to treating the open abdominal cavity 32, the healthcare provider may first put in an open-cavity treatment device 50 as part of an open-cavity treatment subsystem 52. The open-cavity treatment device 50 may be sized initially to fit the particular application. For example, with reference to FIG. 6, the open-cavity treatment device 202 may be cut along visual indicia 214 through the manipulation zones 212 to properly size the dressing. Referring again to FIG. 1, once the open-cavity treatment device 50 is properly sized, the open-cavity treatment device 50 is placed within the abdominal cavity 32 and on top of the abdominal contents 46. The encapsulated leg members 90 of the open-cavity treatment device 50 may be tucked and worked into desired locations, e.g., the paracolic gutters 92, 94, pelvic cavity, behind a patient's liver, etc.

The healthcare provider may place the deep-tissue closure device 54 on the first side (or top for the orientation shown) of the open-cavity treatment device 50. The deep-tissue closure device 54, which is part of a deep-tissue closure subsystem 56, may need to be sized by cutting the deep-tissue closure device 54 to a desired size to accommodate the deep-tissue wound. The healthcare provider may help to position layers of tissue, namely fascia 36, on the first side (or top for the orientation shown) of the deep-tissue closure device 54. The manifold 64 may be inserted within the abdominal cavity 32 and on top of a portion of the deep-tissue closure device 54.

The sealing member 66 may then be placed over the opening of the abdominal cavity 32 and on the epidermis 44 to provide a pneumatic seal. This may be done by removing releasable backing from the adhesive 70 and then placing the adhesive 70 against the epidermis 44. Then, to help provide additional closing force and support, the surface-wound closure subsystem 60 may be applied. Any of numerous possible embodiments of a surface-wound closure subsystem may be used. In addition, various other subsystems and alternatives might be used as part of the reduced-pressure, abdominal treatment system 30.

With reference still to FIG. 1, the first attachment member 186 may be applied on one side of the surface-wound edges 182 and a second attachment member 193 may be applied generally at a position opposite the first attachment member 186 and on the other side of surface-wound edge 182. The attachment members 186 and 193 may be attached by removing releasable backing from an adhesive layer, e.g., first adhesive 192 on the first attachment member 186, and applying the adhesive against the sealing member 66.

A portion of the reduced-pressure interface 72 may then be placed into opening 187 of the surface surface-wound closure subsystem 60 and into the manifold 64. The first reduced-pressure delivery conduit 76 may be fluidly coupled to the reduced-pressure interface 72 and to the reduced-pressure supply subsystem 62, which delivers reduced pressure to the first reduced-pressure delivery conduit 76. The surface surface-wound closure subsystem 60 includes at least one second reduced-pressure interface 194, which is fluidly coupled to a second reduced-pressure delivery conduit 195. The second reduced-pressure delivery conduit 195 is fluidly coupled to the reduced-pressure supply subsystem 62, which delivers a reduced pressure into the second reduced-pressure delivery conduit 195.

The healthcare provider may then activate the reduced-pressure supply subsystem 62, which delivers reduced pressure (a first reduced pressure or treatment-reduced-pressure) to the reduced-pressure treatment subsystem 58 and in particular to the manifold 64. This reduced pressure is also communicated to the open-cavity treatment device 50 and the deep-tissue closure device 54. As suggested by the embodiment of FIG. 28, reduced pressure might also be supplied to the surface-wound closure subsystem 60 by the manifold 64, but in the illustrative embodiment of FIG. 1, reduced pressure (a second reduced pressure or closing-reduced-pressure) is supplied by the second reduced-pressure delivery conduit 195 to the sealed contracting member 196 causing the sealed contracting member 196 to contract and pull the surface-wound edges 182 of the epidermis 44 together.

The reduced-pressure, abdominal treatment system 30, and particularly the open-cavity treatment device 50, helps remove ascites and other fluids from the abdominal cavity 32 and the tissue site 34 without adhering to the abdominal contents 46. The reduced-pressure, abdominal treatment system 30 utilizes the deep-tissue closure subsystem 56 to help close the fascia 36 without the fascia "rolling" or causing other problems and without requiring puncture wounds to the fascia 36. The reduced-pressure, abdominal treatment system 30 helps generally to provide reduced-pressure treatment within the abdominal cavity 32 by way of the reduced-pressure treatment subsystem 58, which includes the manifold 64. The reduced-pressure, abdominal treatment system 30 also helps close the surface wound 180 in the epidermis 44 by using the surface surface-wound closure subsystem 60.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in a connection to any one embodiment may also be applicable to any other embodiment.

We claim:

1. A method of manufacturing a system for treating an abdominal cavity of a patient, the method comprising the steps of:
   forming an open-cavity treatment device comprising a plurality of encapsulated leg members for providing reduced-pressure treatment to a patient's abdominal cavity, wherein each of the plurality of encapsulated leg members comprises a leg manifold member disposed within an interior portion of the encapsulated leg member and is formed with fenestrations operable to allow fluid flow into the interior portion;
   forming a deep-tissue closure device for applying a closing force on a deep-tissue wound on a patient's fascia and configured to be coupled to the open-cavity treatment device; and
   forming a surface-wound closure subsystem for providing a closing force on a surface wound on a patient's epidermis, wherein the surface-wound closure subsystem is configured to be deployed on an external surface of the patient's epidermis.

2. The method of claim 1 further comprising the steps of providing a reduced-pressure supply subsystem and fluidly coupling the reduced-pressure supply subsystem to the open-cavity treatment device, the deep-tissue closure device, and the surface-wound closure subsystem.

3. The method of claim 1, wherein the step of forming an open-cavity treatment device further comprises the steps of:
   forming a non-adherent drape with fenestrations;
   coupling the plurality of encapsulated leg members to the non-adherent drape;
   forming a central connection member with a connection manifold member; and
   coupling the central connection member to the non-adherent drape and to the plurality of encapsulated leg members, wherein each leg manifold member is in fluid communication with the connection manifold member.

4. The method of claim 3 wherein the step of forming a non-adherent drape comprises forming an elastomeric drape, forming fenestrations on the elastomeric drape, and placing visual indicia on the elastomeric drape that indicates various sizes that might be cut.

5. The method of claim 1, wherein the step of forming a deep-tissue closure device comprises the steps of:
   forming a contractible matrix having a first side and a second, inward-facing side, the first side formed with a plurality of apertures, and the second, inward-facing side formed with a plurality of cells, and further formed with a plurality of inter-cellular apertures, the contractible matrix for disposing proximate the deep-tissue wound;
   providing a manifold member operable to distribute reduced pressure; and
   providing a sealing member operable to provide a pneumatic seal over the patient's abdominal cavity.

6. The method of claim 1, wherein the step of forming a surface-wound closure subsystem comprises the steps of:
   forming a first attachment member for releasably attaching to a first portion of the patient's epidermis proximate an edge of the surface wound;
   forming a second attachment member for releasably attaching to a second portion of the patient's epidermis proximate the edge of the surface wound; and
   forming a sealed contracting member operable to contract when placed under reduced pressure.

7. The method of claim 1, wherein the step of forming a surface-wound closure subsystem comprises the steps of:
   forming a sealed contracting member;
   forming a plurality of attachment-base members, each attachment-base member having a base and a first wall having a first end and a second end, the first end of the first wall having a first movable connection member and the second end of the first wall having a second movable connection member, each attachment-base member for releasably attaching to a portion of the patient's epidermis and for coupling to the sealed contracting member;
   forming a plurality of connecting members, each connecting member having a second wall with a first end and a second end, the first end of the second wall having a third movable connection member and the second end of the second wall having a fourth movable connection member, each connecting member for moveably coupling to one of the plurality of attachment-base members;
   fluidly coupling a reduced-pressure interface to the sealed contracting member, the reduced-pressure interface operable to deliver reduced pressure to the sealed contracting member; and
   wherein the plurality of attachment-base members and the plurality of connecting members are operable to moveably couple to form a circumferential wall defining an interior space and wherein the sealed contracting member is to be disposed within the interior space.

8. The method of claim 1, wherein the step of forming a surface-wound closure subsystem comprises the steps of:
   forming a flexible strap operable to be formed into a closed loop; and
   forming a plurality of modular closing members, wherein the step of forming a plurality of modular closing members comprises, for each of the plurality of modular closing members, the steps of:
   forming an attachment member for releasably attaching to a portion of the patient's epidermis proximate an edge of the surface wound, the attachment member formed with a base and a wall,
   forming a sealed contracting member having a first end and a second end, wherein the sealed contracting member is operable to contract when placed under reduced pressure,
   coupling the second end of the sealed contracting member to the attachment member,
   forming a connection member, the connection member operable to selectively couple to the flexible strap,
   coupling the connection member to the first end of the sealed contracting member, and
   forming a reduced-pressure interface fluidly coupled to the sealed contracting member for delivering reduced pressure to the sealed contracting member.

9. A method of manufacturing an abdominal treatment system, the method comprising the steps of:
   forming an open-cavity treatment device for providing reduced-pressure treatment proximate a patient's abdominal contents, the open-cavity treatment device comprising a central connection member, a non-adherent drape, and a plurality of encapsulated leg members coupled to the central connection member and to the non-adherent drape, each of the plurality of encapsulated leg members having an interior portion and a leg manifold member disposed within the interior portion, and being formed with fenestrations operable to allow fluid flow into the interior portion;
   forming a deep-tissue closure device adapted to be deployed proximate to the open-cavity treatment device for applying a closing force on a deep-tissue wound on a patient's fascia, the deep-tissue closure device having a contractible matrix; and providing a reduced-pressure treatment subsystem for providing reduced pressure to the open-cavity treatment device and the deep-tissue closure device;

wherein each of the leg manifold members comprise a plurality of interconnected flow channels.

10. The method of claim 9 further comprising the step of forming a surface-wound closure subsystem for providing a closing force on a surface wound on a patient's epidermis, wherein the step of forming a surface-wound closure subsystem comprises the steps of:

forming a first attachment member for releasably attaching to a first portion of the patient's epidermis proximate an edge of the surface wound;

forming a second attachment member for releasably attaching to a second portion of the patient's epidermis proximate the edge of the surface wound; and forming a sealed contracting member operable to contract when placed under reduced pressure.

11. The method of claim 10 further comprising the step of:

forming a third attachment member for releasably attaching to a third portion of the patient's epidermis proximate the edge of the surface wound, wherein the third attachment member is spaced from the first and second attachment members; and wherein the third attachment member is coupled to the sealed contracting member.

12. The method of claim 11 further comprising the step of:

forming a fourth attachment member for releasably attaching to a fourth portion of the patient's epidermis proximate the edge of the surface wound, wherein the fourth attachment member is spaced from the first, second, and third attachment members; and wherein the fourth attachment member is coupled to the sealed contracting member.

13. The method of claim 10 wherein:

the step of forming a first attachment member further comprises the step of coupling a first base member to a first adhesive; and the step of forming a second attachment member further comprises the step of coupling a second base member to a second adhesive.

14. The method of claim 10 wherein the step of forming a sealed contracting member comprises the steps of:

providing a contracting manifold material having a first side and a second, inward-facing side, and a peripheral edge;

disposing a first sealing member against the first side of the contracting manifold material;

disposing a second sealing member against the second, inward-facing side of the contracting manifold material;

disposing a peripheral sealing device against the peripheral edge of the contracting manifold material; and wherein the first sealing member, the second sealing member, and the peripheral sealing device are operable to pneumatically seal the contracting manifold material.

15. The method of claim 14 wherein the peripheral sealing device comprises a third sealing member.

16. The method of claim 14 wherein the peripheral sealing device comprises an outer wall.

17. A method of manufacturing an abdominal treatment system, the method comprising the steps of:

forming an open-cavity treatment device for providing reduced-pressure treatment proximate a patient's abdominal contents, the open-cavity treatment device comprising a central connection member, a non-adherent drape, and a plurality of encapsulated leg members coupled to the central connection member and to the non-adherent drape;

forming a deep-tissue closure device adapted to be deployed proximate to the open-cavity treatment device for applying a closing force on a deep-tissue wound on a patient's fascia, the deep-tissue closure device having a contractible matrix; and forming a surface-wound closure subsystem for providing a closing force on a surface wound on a patient's epidermis, the surface-wound closure subsystem comprising a sealed contracting member, a plurality of attachment-base members, a plurality of connecting members, wherein the plurality of attachment-base members and the plurality of connecting members are operable to moveably couple to form a circumferential wall defining an interior space and wherein the sealed contracting member is to be disposed within the interior space.

18. The method of claim 17, the method further comprising the step of providing a reduced-pressure treatment subsystem for providing reduced-pressure treatment in the patient's abdominal cavity.

19. The method of claim 18, wherein the step of providing a reduced-pressure treatment subsystem comprises fluidly coupling a reduced-pressure interface to the sealed contracting member by coupling at least one reduced-pressure interface member to at least one attachment-base member.

20. The method of claim 17, further comprising the steps of:

coupling the plurality of attachment-base members to the sealed contracting member; and coupling the plurality of connecting members to the sealed contracting member.

21. A method of manufacturing a system for treating an abdominal cavity of a patient, comprising:

forming an open-cavity treatment device comprising a plurality of encapsulated leg members for providing reduced-pressure treatment to a patient's abdominal cavity, wherein each of the plurality of encapsulated leg members has an interior portion with a leg manifold member and is formed with fenestrations operable to allow fluid flow into the interior portion, and further comprising the steps of:

forming a non-adherent drape with fenestrations, coupling the plurality of encapsulated leg members to the non-adherent drape, forming a central connection member with a connection manifold member, and coupling the central connection member to the non-adherent drape and to the plurality of encapsulated leg members, wherein each leg manifold member is in fluid communication with the connection manifold member;

forming a deep-tissue closure device for applying a closing force on a deep-tissue wound on a patient's fascia and configured to be coupled to the open-cavity treatment device; and forming a surface-wound closure subsystem for providing a closing force on a surface wound on a patient's epidermis, wherein the surface-wound closure subsystem is configured to be deployed on an external surface of the patient's epidermis.

22. The method of claim 21, wherein the step of forming a non-adherent drape comprises forming an elastomeric drape, forming fenestrations on the elastomeric drape, and placing visual indicia on the elastomeric drape that indicates various sizes that might be cut.

* * * * *